United States Patent
Leitgeb et al.

(10) Patent No.: US 8,652,795 B2
(45) Date of Patent: Feb. 18, 2014

(54) MUTANT LACTATE OXIDASE WITH INCREASED STABILITY AND PRODUCT, METHODS AND USES INVOLVING THE SAME

(71) Applicants: Stefan Leitgeb, Graz (AT); Thomas Meier, Munich (DE); Bernd Nidetzky, Graz (AT); Bernhard Schaffar, Graz (AT); Thomas Stoisser, Graz (AT)

(72) Inventors: Stefan Leitgeb, Graz (AT); Thomas Meier, Munich (DE); Bernd Nidetzky, Graz (AT); Bernhard Schaffar, Graz (AT); Thomas Stoisser, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/622,209

(22) Filed: Sep. 18, 2012

(65) Prior Publication Data
US 2013/0071868 A1   Mar. 21, 2013

(30) Foreign Application Priority Data

Sep. 20, 2011   (EP) .................................. 11007657

(51) Int. Cl.
*C12Q 1/26* (2006.01)
*C12N 9/04* (2006.01)
*G01N 33/53* (2006.01)

(52) U.S. Cl.
USPC ............................. 435/25; 435/190; 435/7.91

(58) Field of Classification Search
None
See application file for complete search history.

(56) References Cited

U.S. PATENT DOCUMENTS 6,652,720 B1 * 11/2003 Mansouri et al. ........ 204/403.11

FOREIGN PATENT DOCUMENTS

JP   10-248574   *   9/1998

OTHER PUBLICATIONS

UniProt Accession No. F4BMZ4, Jun. 2011, 1 page.*
Toda et al., "Gene cloning, purification, and characterization of a lactate oxidase from *Lactococcus lactis* subsp. cremoris IFO3427", J. Ferment. Bioengineer. 85:507-510, 1998.*
Hirotaka Minagawa, et al., "Effect of mutations at Glu160 and Val198 on the thermostability of lactate oxidase," Eur. J. Biochem. 270, 3628-3633, 2003.
Kazuko Yorita, et al., "Conversion of L-Lactate Oxidase to a Long Chain α-Hydroxyacid Oxidase by Site-directed Mutagenesis of Alanine 95 to Blycine," The Journal of Biological Chemistry, vol. 271, No. 45, pp. 28300-28305, Nov. 1996.
Hirotaka Minagawa, et al., "Thermostabilization of Lactate Oxidase by Random Mutagenesis," Biotechnology Letters, vol. 17, No. 9, pp. 975-980, Sep. 1995.

* cited by examiner

*Primary Examiner* — David J Steadman
(74) *Attorney, Agent, or Firm* — Faegre Baker Daniels LLP

(57) ABSTRACT

The present disclosure relates to a mutant lactate oxidase having increased stability, a nucleic acid encoding the mutant lactate oxidase, an expression vector comprising the nucleic acid, a host cell comprising the nucleic acid or the expression vector, a method of determining lactate in a sample, the use of the mutant lactate oxidase for determining lactate, a device for determining lactate in a sample using the mutant lactate oxidase and a kit for determining lactate comprising the mutant lactate oxidase.

16 Claims, 3 Drawing Sheets

MUTANT LACTATE OXIDASE WITH INCREASED STABILITY AND PRODUCT, METHODS AND USES INVOLVING THE SAME

PRIORITY CLAIM

This application claims the benefit of European Patent Application Number EP 11007657.7 filed on Sep. 20, 2011, which is incorporated herein by reference in its entirety.

BACKGROUND

The present disclosure relates to a mutant lactate oxidase having increased stability, a nucleic acid encoding the mutant lactate oxidase, an expression vector comprising the nucleic acid, a host cell comprising the nucleic acid or the expression vector, a method of determining lactate in a sample, the use of the mutant lactate oxidase for determining lactate, a device for determining lactate in a sample using the mutant lactate oxidase and a kit for determining lactate comprising the mutant lactate oxidase.

Lactic acid, also known as milk acid, plays a role in several biochemical processes. Lactic acid is an alpha hydroxy acid with the chemical formula $C_3H_6O_3$. In solution it is present in its ionic form, i.e., as lactate $CH_3CH(OH)COO^-$. Lactate is chiral and has two optical isomers. One is known as L-(+)-lactate or (S)-lactic acid and the other is D-(−)-lactic acid or (R)-lactic acid. L-(+)-lactic acid is the biologically important isomer.

In animals (including humans), L-lactate is constantly produced from pyruvate via the enzyme lactate dehydrogenase (LDH) during normal metabolism and exercise. It normally does not increase in concentration until the rate of lactate production exceeds the rate of lactate removal, which is governed by a number of factors, including monocarboxylate transporters, concentration and isoform of LDH, and oxidative capacity of tissues. In humans, the concentration of blood lactate is usually 1-2 mmol/L at rest, but can rise to over 20 mmol/L during intense exertion.

The lactate concentration or lactate to pyruvate ratio reflects the redox state. Monitoring lactate levels is, therefore, a good indicator of the balance between tissue oxygen demand and utilization and is useful when studying cellular and animal physiology. Accordingly, lactate in biological samples such as serum, plasma, blood, urine, and saliva or intracellular and extracellular lactate concentrations in cell culture samples may be monitored in order to study or monitor a subject's or cell's condition.

Determinations of blood lactate levels are frequently done in the context of competitive sports, fitness, and rehabilitation, these determinations are used to:

assess the intensity of individual exercise routines;
improve various phases of exercise and recovery; and
reduce of the risk of overload and injury.

As detailed above, anaerobic glycolysis markedly increases blood lactate, especially with prolonged exercise.

In medicine, the determination of lactate levels in a patent may be used to:

assay for tissue hypoxia; and
estimate the severity of disease and prognosis, in so far as it is reflected by abnormal levels of lactate measured in a patient.

For example, lactate concentrations can be increased in any condition that decreases the amount of oxygen available to the body, increases lactate production, and/or decreases lactate clearance. This can be anything from localized increases of lactate in muscle due to strenuous exercise up to life-threatening systemic shock. Excess lactate may be present in a range of diseases, infections, and inherited metabolic and mitochondrial disorders. The common cause for increased blood lactate is anoxia resulting from conditions such as shock, pneumonia and congestive heart failure. Lactic acidosis may also occur in renal failure and leukemia. Also, thiamine deficiency and diabetic ketoacidosis are associated with increased levels of lactate. They may also be caused by certain medications, such as metformin (taken by diabetics) and isoniazid (tuberculosis treatment).

Tests for the determination of lactate are known in the art. In recent years, enzymatic methods for the determination of lactate have been developed. Enzymatic methods involve the use of an enzyme in the determination method, are generally simple and provide greater specificity, accuracy, and reproducibility than non-enzymatic. The first enzymatic method described for the determination of lactate was based on the transfer of hydrogen from lactate to potassium ferricyanide by lactate dehydrogenase. This procedure was cumbersome and did not receive wide acceptance. Subsequent methods involved the UV measurement of the formation of NADH. In 1974, a lactate procedure was described that measures the amount of NADH formed by the oxidation of lactate catalyzed by lactate dehydrogenase. This method uses hydrazine as a trapping agent for pyruvate. Another method is also based on the catalytic action of lactate dehydrogenase but includes alanine transaminase in the reaction mixture to more rapidly remove the pyruvate formed from the conversion of lactate. Still another method uses an enzymatic reaction to convert lactate to pyruvate involving lactate oxidase. The hydrogen peroxide produced by this reaction may be then used in an enzymatic reaction to generate a colored dye.

The term "lactate oxidase" (classified as EC 1.1.3.15 by the Enzyme Commission of the International Union of Biochemistry) generally means an enzyme that catalyses the oxidation of L-lactate to pyruvate with reduction of $O_2$ to $H_2O_2$ ((S)-2-hydroxy-acid oxidase). Lactate oxidase is a member of a family of FMN (flavin mononucleotide)-dependent alpha hydroxy acid oxidizing enzymes. It employs flavin mononucleotide (FMN) as cofactor. Lactate oxidase enzymes appear in viruses and cellular organisms.

Lactate oxidase from *Aerococcus viridans* is often used in biosensors and in vitro tests in order to detect lactate, e.g., in blood. These biosensors and in vitro tests are predominantly used in the monitoring of, e.g., intensive care patients and athletes. The lifetime of the sensors is determined by the stability of the lactate oxidase which has a finite shelf-life and becomes inactivated during use. The stability of lactate oxidase also influences the shelf-life of lactate oxidase when it is used as a reagent or as part of a device. The stability of lactate oxidase also influences the in-use time of the enzyme when it is used as a reagent for in vitro testing. A variant of lactate oxidase that exhibits greater stability will have a longer shelf-life than a less stable variant. And one can use a more stable variant of lactate oxidase to perform a larger number of assays than one can expect to perform with a less stable variant of the enzyme.

Due to lactate oxidase's limited shelf-life and relatively short half-life when it is used to measure lactate as part of a device such as a sensor or as a reagent in a test, it is frequently necessary to have to substitute the lactate oxidase with additional lactate oxidase in the device or in the assay, as the activity of the enzyme falls below a technically acceptable level. Frequent changes of sensors and test equipment is consumer-unfriendly, a waste of resources and, therefore, to be avoided. Due to the low stability of the wild-type lactate oxidase, determinations involving lactate oxidase are usually carried out at reduced temperature. Accordingly, an additional advantage of a variant of lactate oxidase with increased stability would be that within devices used for applications such example blood analysis it would not be as critical to have a thermostat for maintaining the temperature of the enzyme in, for example, the 25 to 30° C. range. This is especially useful because blood gas analysis (often carried out concomitantly) is usually carried out at 37° C. Accordingly, a more stable lactate oxidase would significantly reduce complexity of devices, thereby providing a basis for low-cost devices, which is of particular relevance, e.g., in so-called emerging markets. Therefore, it is of great interest to find ways to increase stability of the lactate oxidase in order to increase its shelf-life and its in-use time when used in biosensors and in vitro tests.

SUMMARY

It is against the above background that the embodiments of the present disclosure provide certain unobvious advantages and advancements over the prior art. In particular, the inventors have recognized a need for improvements in mutant lactate oxidase products, methods and uses involving same.

Although the embodiments of the present disclosure are not limited to specific advantages or functionality, it is noted that the present disclosure provides a lactate oxidase with increased stability.

In accordance with one embodiment of the present disclosure, a mutant lactate oxidase is provided comprising a functionally active mutant lactate oxidase having an amino acid sequence that: (i) is at least 90% identical to the amino acid sequence of SEQ ID NO: 1 or SEQ ID NO: 2, or a functionally active variant thereof; and (ii) has an amino acid substitution at the position corresponding to position Tyr191 of SEQ ID NO: 1 or SEQ ID NO: 2, wherein the mutant lactate oxidase is more stable than is unsubstituted lactate oxidase.

In accordance with another embodiment of the present disclosure, a nucleic acid is provided comprising: a polynucleotide encoding a functionally active mutant lactate oxidase having an amino acid sequence that: (i) is at least 90% identical to the amino acid sequence of SEQ ID NO: 1 or SEQ ID NO: 2, or a functionally active variant thereof; and (ii) has an amino acid substitution at the position corresponding to position Tyr191 of SEQ ID NO: 1 or SEQ ID NO: 2, wherein the mutant lactate oxidase is more stable than is the unsubstituted lactate oxidase.

In accordance with yet another embodiment of the present disclosure, a method of determining lactate in a sample is provided, comprising the steps of: a) contacting a sample with a functionally active mutant lactate oxidase having an amino acid sequence that: (i) is at least 90% identical to the amino acid sequence of SEQ ID NO: 1 or SEQ ID NO: 2, or a functionally active variant thereof; and (ii) has an amino acid substitution at the position corresponding to position Tyr191 of SEQ ID NO: 1 or SEQ ID NO: 2, wherein the mutant lactate oxidase is more stable than is unsubstituted lactate oxidase; and b) measuring at least one of the following: A. the amount of at least one of the following compounds produced by the functionally active lactate oxidase: pyruvate or $H_2O_2$, and/or B. the amount of $O_2$ consumed by the functionally active mutant lactate oxidase in the presence of lactate.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE FIGURES

The following detailed description of the embodiments of the present disclosure can be best understood when read in conjunction with the following figures.

Figure 1A:
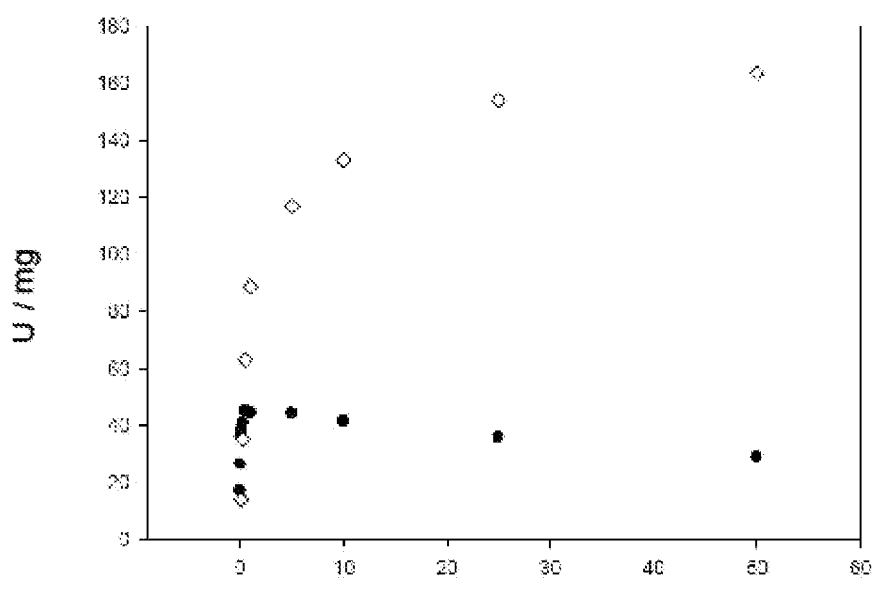
FIG. 1A. A graph illustrating the kinetic characterization of wild-type lactate oxidase (◇) and mutant Tyr191Phe (●). The experiment was carried out as described in Example 1.
Figure 1B:
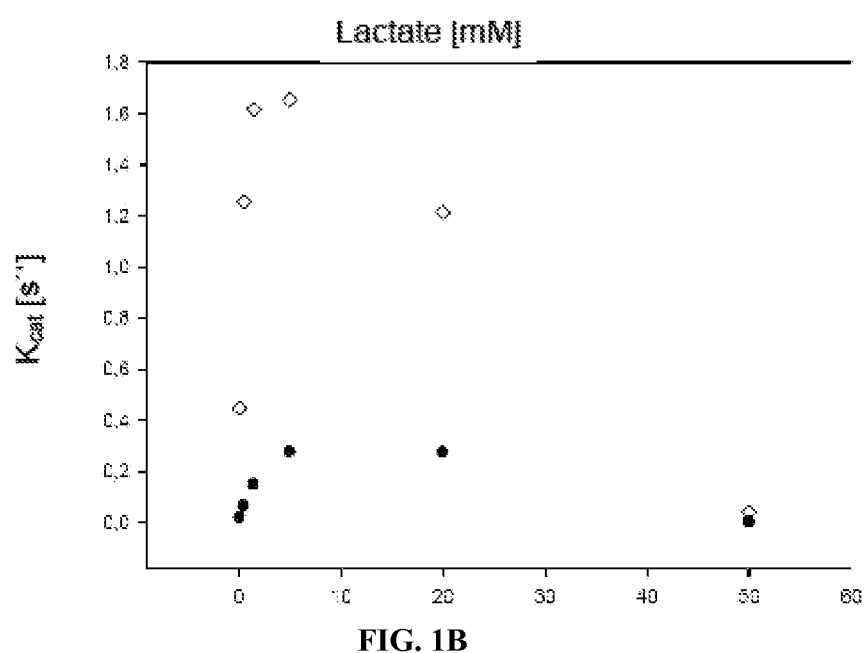
FIG. 1B. A graph illustrating the kinetic characterization of wild-type lactate oxidase (◇) and mutant Ala95Gly (●). The experiment was carried out as described in Example 2.

```
SEQUENCE LISTING
The amino acid sequence of a wild type lactate
oxidase from Aerococcus viridians with a carboxy-terminal
deletion.
                                                              SEQ ID NO: 1
           10         20         30         40         50         60
    MNNNDIEYNA PSEIKYIDVV NTYDLEEEAS KVVPHGGFNY IAGASGDEWT KRANDRAWKH
                                        36

70         80         90        100        110        120
    KLLYPRLAQD VEAPDTSTEI LGHKIKAPFI MAPIAAHGLA HATKEAGTAR AVSEFGTIMS
                                         95        103

130        140        150        160        170        180
    ISAYSGATFE EISEGLNGGP RWFQIYMAKD DQQNRDILDE AKGDGATAII LTADSTVSGN
                                                   160

190        200        210        220        230        240
    RDRDVKNKFV YPFGMPIVQR YLRGTAEGMS LNNIYGASKQ KISPRDIEEI AAHSGLPVFV
             191        198                   212                   232

250        260        270
    KGIQHPEDAD MAIKAGASGI WVSNHGARQL YEAPGS.

The amino acid sequence of a wild type lactate
oxidase from Aerococcus viridians without a carboxy-terminal
deletion.
```

-continued

SEQ ID NO: 2

```
         10         20         30         40         50         60
MNNNDIEYNA PSEIKYIDVV NTYDLEEEAS KVVPHGGFNY IAGASGDEWT KRANDRAWKH
                                     36

70         80         90        100        110        120
KLLYPRLAQD VEAPDTSTEI LGHKIKAPFI MAPIAAHGLA HTTKEAGTAR AVSEFGTIMS
                                     95        103

130        140        150        160        170        180
ISAYSGATFE EISEGLNGGP RWFQIYMAKD DQQNRDILDE AKSDGATAII LTADSTVSGN
                                    160

190        200        210        220        230        240
RDRDVKNKFV YPFGMPIVQR YLRGTAEGMS LNNIYGASKQ KISPRDIEEI AGHSGLPVFV
           191     198                212                  232

250        260        270        280        290        300
KGIQHPEDAD MAIKRGASGI WVSNHGARQL YEAPGSFDTL PAIAERVNKR VPIVFDSGVR
                                    277

310        320        330        340        350        360
RGEHVAKALA SGADVVALGR PVLFGLALGG WQGAYSVLDY FQKDLTRVMQ LTGSQNVEDL

370
KGLDLFDNPY GYEY.
```

A polynucleotide primer used to create a mutant form of
lactate oxidase. Artificial Sequence, Primer Y191Ffw:

SEQ ID NO: 3 tcgttttccc atttggtatg ccgatcgttc aacgttactt acg.

A polynucleotide primer used to create a mutant form of
lactate oxidase. Artificial Sequence, Primer Y191Frev:

SEQ ID NO: 4

GAACGATCGGCATACCAAATGGGAAAACGAATTTATTCTTCAC.

A polynucleotide primer used to create a mutant form of
lactate oxidase. Artificial Sequence, Primer Y191Lfw:

SEQ ID NO: 5

TCGTTCTCCCATTTGGTATGCCGATCGTTCAACGTTACTTACG.

A polynucleotide primer used to create a mutant form of
lactate oxidase. Artificial Sequence, Primer Y191Lrev:

SEQ ID NO: 6

GAACGATCGGCATACCAAATGGGAGAACGAATTTATTCTTCAC.

A polynucleotide primer used to create a mutant form of
lactate oxidase. Artificial Sequence, Primer A95Gfw:

SEQ ID NO: 7

CCAATTGGTGCCCATGGTTTAGCTCACGCTACTAAAGAAGCTGG.

A polynucleotide primer used to create a mutant form of
lactate oxidase. Artificial Sequence, Primer A95Grev:

SEQ ID NO: 8

AGCGTGAGCTAAACCATGGGCACCAATTGGGGCCATGATGAATGG.

DESCRIPTION

Surprisingly, it has been found that a mutation of tyrosine at position 191 of the amino acid sequence of lactate oxidase of SEQ ID NO: 1 increases the stability of lactate oxidase.

A first aspect the present disclosure provides a mutant lactate oxidase having increased stability, comprising an amino acid sequence that:
  (i) is at least 90% identical to the amino acid sequence of SEQ ID NO: 1 or SEQ ID NO: 2 or a functionally active variant thereof; and
  (ii) has an amino acid substitution at the position corresponding to position Tyr191 of SEQ ID NO: 1 or SEQ ID NO: 2.

In some embodiments the functionally active variant of aspect 1 includes at least one further amino acid substitution at a position selected from the group consisting of Gly36, Ala95, Thr103, Glu160, Val198, Asn212, Ala/Gly232 and Phe277 of SEQ ID NO: 1 or SEQ ID NO: 2.

According to the present disclosure, the mutant lactate oxidase has increased stability in comparison to the respective lactate oxidase that is without a mutation at position 191. Surprisingly, it was found that a mutation at position 191, wherein Tyr is substituted with another amino acid, particularly an amino acid with non-polar rather large side groups such as phenylalanine, leucine and tryptophane, increases the stability of the enzyme in the presence of an alkaline environment relative to the wild-type lactate oxidase. Suitable tests for studying stability of an enzyme, particularly depending from the ambient conditions such as media conditions are well-known to the skilled person. A suitable and exemplary test is also described in the Examples, particularly Example 1.

In a typical embodiment of the present disclosure, increased stability of the mutant lactate oxidase relative to the respective lactate oxidase without mutation at position 191 is manifested as increase in half-life of the mutant, e.g., ($t_{1/2}$(mut191)), relative to the half-life of the respective lactate oxidase without mutation at position 191, e.g., ($t_{1/2}$(wild-type191)). The half-life ($t_{1/2}$) of the enzyme indicates the amount of time in which 50% of the original activity (activity at t=0) is lost (see also Example 1 for further illustration) and after which the residual activity amounts to 50%.

Increased stability results in an increased half-life of the mutant relative to the respective lactate oxidase that is without a mutation at position 191. Typically, the half-life is increased by at least 10%, 20%, 30% or 40%, more typically at least 50%, 75% or 100%, still more typically at least 125%, 150%, 175% or 200%, 250%, and most typically 300%. Percentile increase in half-life may be determined using the following for relationship: $[t_{1/2}(mut191)/t_{1/2}(wild-type191)-1]*100$.

The term "SEQ ID NO: 1" as referred to herein denotes the amino acid sequence as shown in SEQ ID NO: 1 and represents the amino acid sequence of a wild type lactate oxidase from *Aerococcus viridians* with a carboxy-terminal deletion but not having Tyr191 mutated. The wild-type lactate oxidase fragment of *Aerococcus viridians* is a 276-amino acid protein. In particular, the term "SEQ ID NO: 1" refers to the amino acid sequence as set forth in the Sequence Listing (please note that substitution sites specified above are indicated by underline and specified by position numbers).

The term "SEQ ID NO: 2" as referred to herein denotes the amino acid sequence as shown in SEQ ID NO: 2 and represents the amino acid sequence of a wild type lactate oxidase from *Aerococcus viridians* not having Tyr191 mutated without a carboxy-terminal deletion. The full length wild-type lactate oxidase of *Aerococcus viridians* is a 374-amino acid protein. Its sequence is also available from UNIPROT database under accession number Q44467 (please note that substitution sites specified above are indicated by underline and specified by position numbers).

Please note that the sequences of SEQ ID NO: 1 and 2 differ in their length as well as the amino acids at positions 102, 163, 232 and 255. In the context of the present disclosure the proteins consisting of SEQ ID NO: 1 or SEQ ID NO: 2 are referred to as wild-type lactate oxidase of *Aerococcus viridians*.

The term "mutant lactate oxidase" relates to a variant of lactate oxidase having an amino acid sequence that is different from the wild-type sequence of lactate oxidase from *Aerococcus viridians*, i.e., SEQ ID NO: 1 or 2. With respect to the mutant lactate oxidase of the present disclosure it is noted that the mutant is functionally active. This means that the mutant has maintained its biological function, i.e., the enzymatic activity of a lactate oxidase. However, the activity of the mutant may be reduced or increased relative to the wild-type (see also Example 1).

The activity of an enzyme may be expressed as in units (U). One U is defined as the amount of the enzyme that catalyzes the conversion of 1 micro mole of substrate per minute. The conditions also have to be specified: one usually takes a temperature of 37° C. and the pH value and substrate concentration that yield the maximal substrate conversion rate. The skilled person will understand that the mutant should maintain a minimal activity, typically of at least 5 U/mg enzyme, more typically 20 U/mg enzyme.

Typically, maintenance of biological function is defined as having at least 10%, 20%, 30% or 50%, or at least 60%, more typically at least 70%, 80% or 90%, still more typically 95% of the activity of the lactate oxidase of SEQ ID NO: 1 or 2. The biological activity may be determined by any method known to the skilled person, for example as described in Examples 1 and 2.

The mutant lactate oxidase according to the present disclosure is inter alia defined by having an amino acid substitution at the position corresponding to position Tyr191 of SEQ ID NO: 1 or 2. This means that the amino acid Tyr at position 191 of SEQ ID NO: 1 or 2 is substituted with another amino acid. Tyrosine (also referred to as 4-hydroxyphenylalanine) has a polar side group. In the Examples, Tyr191 has been substituted with phenylalanine or leucine, i.e., an amino acids with a non-polar side group. Due to the similarity of phenylalanine to tryptophane (also an amino acid with a non-polar, hydrophobic, aromatic side-chain) and leucine to isoleucine, it is clear that substitution of Tyr191 with Trp or Ile will also provide the desired effect, namely a lactate oxidase that exhibits increased stability. Furthermore, it is assumed that this is also true for other amino acids with non-polar side groups such as glycine, alanine, valine, leucine, isoleucine, proline, and methionine. Due to their relative sizes, this should be particularly true for the amino acids isoleucine, proline, and methionine.

The term "at least 90% identical" or "at least 90% sequence identity" as used herein means that the sequence of the mutant lactate oxidase according to the present disclosure has an amino acid sequence characterized in that, within a stretch of 100 amino acids, at least 90 amino acids residues are identical to the sequence of the corresponding wild-type sequence. In a typical embodiment of the present disclosure, the amino acid sequence of the mutant is at least 91%, 92%, 93% or 94% identical to the amino acid sequence of SEQ ID NO: 1 or 2, or a functionally active variant thereof, more typically at least 95% or 96%, still more typically at least 97% or 98%, or 99% identical. Sequence identity according to the present disclosure can, e.g., be determined by methods of sequence alignment in the form of sequence comparison. Methods of sequence alignment are well known in the art and include various programs and alignment algorithms which have been described in, e.g., Pearson and Lipman ("Improved tools for biological sequence comparison", *Proc Natl Acad Sci USA*. 1988 April; 85(8):2444-8). Moreover, the NCBI Basic Local Alignment Search Tool (BLAST) is available from several sources, including the National Center for Biotechnology Information (NCBI, Bethesda, Md.).

In another embodiment the mutant is 100% identical to the sequence of SEQ ID NO: 1 or 2 apart from the mutation at position Tyr191 and optionally the at least one further amino acid substitution at a position selected from the group consisting of Gly36, Ala95, Thr103, Glu160, Val198, Asn212, Ala/Gly232 and Phe277. In yet another embodiment the mutant is 100% identical to the sequence of SEQ ID NO: 1 or 2 apart from the mutation at position Tyr191 (typically Tyr191Phe or Tyr191Leu) and optionally one further amino acid substitution at position Ala95 (typically Ala95Gly).

In one embodiment of the present disclosure, the mutant lactate oxidase according to the present disclosure may comprise one or more amino acid deletion(s), particularly small (e.g., up to 10 amino acids) N- and/or C-terminal deletions.

In another embodiment, the sequence of the mutant lactate oxidase according to the present disclosure may comprise, in addition to the substitution at position Tyr191 of SEQ ID NO: 1 or 2 and optionally to the at least one further amino acid substitution at a position selected from the group consisting of Gly36, Ala95, Thr103, Glu160, Val198, Asn212, Ala/Gly232 and Phe277, one or more additional amino acid substitution(s), particularly one or more conservative amino acid substitutions. Examples of conservative amino acid substitutions include those listed below:

| Original Residue | Conservative Substitutions |
|---|---|
| Ala | Ser |
| Arg | Lys |
| Asn | Gln; His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Asn |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In one embodiment of the present disclosure, the mutant lactate oxidase according to the present disclosure may comprise one or more amino acid addition(s), particularly small (e.g., up to 10 amino acids) internal amino acid additions.

In another embodiment, the sequence of the mutant lactate oxidase according to the present disclosure may comprise, in addition to the substitution at position Tyr191 of SEQ ID NO: 1 or 2 and optionally to the at least one further amino acid substitution at a position selected from the group consisting of Gly36, Ala95, Thr103, Glu160, Val198, Asn212, Ala/Gly232 and Phe277, a combination of one or more deletion(s), substitution(s) or addition(s) as defined above.

In the context of the present disclosure, the functionally active variant of amino acid sequence of SEQ ID NO: 1 or 2 is characterized by having at least one, i.e., one, two, three, four, five, six, seven or eight, amino acid substitution(s) at the following positions of SEQ ID NO: 1 or 2: Gly36, Ala95, Thr103, Glu160, Val198, Asn212, Ala/Gly232 and Phe277.

Particularly, any of the amino acids listed is substituted with one alternative amino acid, respectively. Illustrative examples of variants of SEQ ID NO: 1 or 2 include those differing from the amino acids sequence of SEQ ID NO: 1 or 2 by the following substitutions:

Ala95Gly, Thr103Ser, Glu160Gly, Val198Ile, Asn212Asp and Ala/Gly232Ser;
Ala95Ser, Thr103Ser, Glu160Ala, Val198Leu, Asn212Glu and Ala/Gly232Thr;
Gly36Ser, Ala95Gly, Ala/Gly232Ser and Phe277Tyr;
Ala95Gly, Thr103Ser, Glu160Gly, Val198Ile, Asn212Asp, Ala/Gly232Ser and Phe277Tyr;
Gly36Ser, Thr103Ser, Glu160Gly, Val198Ile, Asn212Asp, Ala/Gly232Ser and Phe277Tyr; or
Gly36Ser, Ala95Gly, Thr103Ser, Glu160Gly, Val198Ile, Asn212Asp, Ala/Gly232Ser and Phe277Tyr.

Substitutions at position Gly36, Thr103, Glu160, Val198, Asn212, Ala/Gly232 and Phe277 have been shown to confer increased thermal stability to mutant lactate oxidases (see U.S. Pat. No. 5,656,471, U.S. Pat. No. 7,416,871 B2). Accordingly, it is advantageous to combine stability towards alkaline (i.e., at pH values>7) conditions (mutation of Tyr191) with increased thermal stability.

Substitutions at position Ala95 have been shown to improve substrate specificity (see Yorita, et al., J. Biol. Chem., 1996, 45, 28300-28305 and Example 2). Accordingly, it is advantageous to combine stability (mutation of Tyr191) and optionally increased thermal stability (Gly36, Thr103, Glu160, Val198, Asn212, Ala/Gly232 and/or Phe277) with improved substrate specificity (mutation of Ala95).

Please note that amino acid Phe277 is only present in SEQ ID NO: 2 and, therefore, amino acid substitution Phe277 relates to SEQ ID NO: 2.

Additionally, sequences of SEQ ID NO: 1 and 2 differ in the amino acids at positions 232, wherein SEQ ID NO: 1 and 2 have—at that position—Ala and Gly, respectively. Accordingly, if Ala/Gly232 relates to SEQ ID NO: 1 it means that Ala at position 232 is substituted and if Ala/Gly232 relates to SEQ ID NO: 2 it means that Gly at position 232 is substituted.

Accordingly, the functionally active variant may be characterized by being identical to SEQ ID NO: 1 or 2 apart from:

(i) an amino acid substitution at the position corresponding to position Tyr191; and
(ii) one or more amino acid substitution(s) at the following position(s):
Gly36,
Ala95,
Thr103,
Glu160,
Val198,
Asn212,
Ala/Gly232,
Phe277,
Gly36 and Ala95,
Gly36 and Thr103,
Gly36 and Glu160,
Gly36 and Val198,
Gly36 and Asn212,
Gly36 and Ala/Gly232,
Gly36 and Phe277,
Ala95 and Thr103,
Ala95 and Glu160,
Ala95 and Val198,
Ala95 and Asn212,
Ala95 and Ala/Gly232,
Ala95 and Phe277,
Thr103 and Glu160,
Thr103 and Val198,
Thr103 and Asn212,
Thr103 and Ala/Gly232,
Thr103 and Phe277,
Glu160 and Val198,
Glu160 and Asn212,
Glu160 and Ala/Gly232,
Glu160 and Phe277,
Val198 and Asn212,
Val198 and Ala/Gly232,
Val198 and Phe277,
Asn212 and Ala/Gly232,
Asn212 and Phe277,
Ala/Gly232 and Phe277,
Gly36, Ala95 and Thr103,
Gly36, Ala95 and Glu160,
Gly36, Ala95 and Val198,
Gly36, Ala95 and Asn212,
Gly36, Ala95 and Ala/Gly232,
Gly36, Ala95 and Phe277,
Gly36, Thr103 and Glu160,
Gly36, Thr103 and Val198,
Gly36, Thr103 and Asn212,
Gly36, Thr103 and Ala/Gly232,
Gly36, Thr103 and Phe277,
Gly36, Glu160 and Val198,
Gly36, Glu160 and Asn212,
Gly36, Glu160 and Ala/Gly232, Gly36, Glu160 and Phe277,
Gly36, Val198 and Asn212,
Gly36, Val198 and Ala/Gly232,
Gly36, Val198 and Phe277,
Gly36, Asn212 and Ala/Gly232,
Gly36, Asn212 and Phe277,
Gly36, Ala/Gly232 and Phe277,
Ala95, Thr103 and Glu160,
Ala95, Thr103 and Val198,
Ala95, Thr103 and Asn212,
Ala95, Thr103 and Ala/Gly232,
Ala95, Thr103 and Phe277,
Ala95, Glu160 and Val198,
Ala95, Glu160 and Asn212,
Ala95, Glu160 and Ala/Gly232,
Ala95, Glu160 and Phe277,
Ala95, Val198 and Asn212,
Ala95, Val198 and Ala/Gly232,
Ala95, Val198 and Phe277,
Ala95, Asn212 and Ala/Gly232,
Ala95, Asn212 and Phe277,
Ala95, Ala/Gly232 and Phe277,
Thr103, Glu160 and Val198,
Thr103, Glu160 and Asn212,
Thr103, Glu160 and Ala/Gly232,
Thr103, Glu160 and Phe277,
Thr103, Val198 and Asn212,
Thr103, Val198 and Ala/Gly232,
Thr103, Val198 and Phe277,
Thr103, Asn212 and Ala/Gly232,
Thr103, Asn212 and Phe277,
Thr103, Ala/Gly232 and Phe277,
Glu160, Val198 and Asn212,
Glu160, Val198 and Ala/Gly232,
Glu160, Val198 and Phe277,
Glu160, Asn212 and Ala/Gly232,
Glu160, Asn212 and Phe277,
Glu160, Ala/Gly232 and Phe277,
Val198, Asn212 and Ala/Gly232,
Val198, Asn212 and Phe277,
Val198, Ala/Gly232 and Phe277,
Asn212, Ala/Gly232 and Phe277,
Gly36, Ala95, Thr103 and Glu160,
Gly36, Ala95, Thr103 and Val198,
Gly36, Ala95, Thr103 and Asn212,
Gly36, Ala95, Thr103 and Ala/Gly232,
Gly36, Ala95, Thr103 and Phe277,
Gly36, Ala95, Glu160 and Val198,
Gly36, Ala95, Glu160 and Asn212,
Gly36, Ala95, Glu160 and Ala/Gly232,
Gly36, Ala95, Glu160 and Phe277,
Gly36, Ala95, Val198 and Asn212,
Gly36, Ala95, Val198 and Ala/Gly232,
Gly36, Ala95, Val198 and Phe277,
Gly36, Ala95, Asn212 and Ala/Gly232,
Gly36, Ala95, Asn212 and Phe277,
Gly36, Ala95, Ala/Gly232 and Phe277,
Gly36, Thr103, Glu160 and Val198,
Gly36, Thr103, Glu160 and Asn212,
Gly36, Thr103, Glu160 and Ala/Gly232,
Gly36, Thr103, Glu160 and Phe277,
Gly36, Thr103, Val198 and Asn212,
Gly36, Thr103, Val198 and Ala/Gly232,
Gly36, Thr103, Val198 and Phe277,
Gly36, Thr103, Asn212 and Ala/Gly232,
Gly36, Thr103, Asn212 and Phe277,
Gly36, Thr103, Ala/Gly232 and Phe277,
Gly36, Glu160, Val198 and Asn212,
Gly36, Glu160, Val198 and Ala/Gly232,
Gly36, Glu160, Val198 and Phe277,
Gly36, Glu160, Asn212 and Ala/Gly232,
Gly36, Glu160, Asn212 and Phe277,
Gly36, Glu160, Ala/Gly232 and Phe277,
Gly36, Val198, Asn212 and Ala/Gly232,
Gly36, Val198, Asn212 and Phe277,
Gly36, Val198, Ala/Gly232 and Phe277,
Gly36, Asn212, Ala/Gly232 and Phe277,
Ala95, Thr103, Glu160 and Val198,
Ala95, Thr103, Glu160 and Asn212,
Ala95, Thr103, Glu160 and Ala/Gly232,
Ala95, Thr103, Glu160 and Phe277,
Ala95, Thr103, Val198 and Asn212,
Ala95, Thr103, Val198 and Ala/Gly232,
Ala95, Thr103, Val198 and Phe277,
Ala95, Thr103, Asn212 and Ala/Gly232,
Ala95, Thr103, Asn212 and Phe277,
Ala95, Thr103, Ala/Gly232 and Phe277,
Ala95, Glu160, Val198 and Asn212,
Ala95, Glu160, Val198 and Ala/Gly232,
Ala95, Glu160, Val198 and Phe277,
Ala95, Glu160, Asn212 and Ala/Gly232,
Ala95, Glu160, Asn212 and Phe277,
Ala95, Glu160, Ala/Gly232 and Phe277,
Ala95, Val198, Asn212 and Ala/Gly232,
Ala95, Val198, Asn212 and Phe277,
Ala95, Val198, Ala/Gly232 and Phe277,
Ala95, Asn212, Ala/Gly232 and Phe277,
Thr103, Glu160, Val198 and Asn212,
Thr103, Glu160, Val198 and Ala/Gly232,
Thr103, Glu160, Val198 and Phe277,
Thr103, Glu160, Asn212 and Ala/Gly232,
Thr103, Glu160, Asn212 and Phe277,
Thr103, Glu160, Ala/Gly232 and Phe277,
Thr103, Val198, Asn212 and Ala/Gly232,
Thr103, Val198, Asn212 and Phe277,
Thr103, Val198, Ala/Gly232 and Phe277,
Thr103, Asn212, Ala/Gly232 and Phe277,
Glu160, Val198, Asn212 and Ala/Gly232,
Glu160, Val198, Asn212 and Phe277,
Glu160, Val198, Ala/Gly232 and Phe277,
Glu160, Asn212, Ala/Gly232 and Phe277,
Val198, Asn212, Ala/Gly232 and Phe277,
Gly36, Ala95, Thr103, Glu160 and Val198,
Gly36, Ala95, Thr103, Glu160 and Asn212,
Gly36, Ala95, Thr103, Glu160 and Ala/Gly232,
Gly36, Ala95, Thr103, Glu160 and Phe277,
Gly36, Ala95, Thr103, Val198 and Asn212,
Gly36, Ala95, Thr103, Val198 and Ala/Gly232,
Gly36, Ala95, Thr103, Val198 and Phe277,
Gly36, Ala95, Thr103, Asn212 and Ala/Gly232,
Gly36, Ala95, Thr103, Asn212 and Phe277,
Gly36, Ala95, Thr103, Ala/Gly232 and Phe277,
Gly36, Ala95, Glu160, Val198 and Asn212,
Gly36, Ala95, Glu160, Val198 and Ala/Gly232,
Gly36, Ala95, Glu160, Val198 and Phe277,
Gly36, Ala95, Glu160, Asn212 and Ala/Gly232,
Gly36, Ala95, Glu160, Asn212 and Phe277,
Gly36, Ala95, Glu160, Ala/Gly232 and Phe277,
Gly36, Ala95, Val198, Asn212 and Ala/Gly232,
Gly36, Ala95, Val198, Asn212 and Phe277,
Gly36, Ala95, Val198, Ala/Gly232 and Phe277,
Gly36, Ala95, Asn212, Ala/Gly232 and Phe277,
Gly36, Thr103, Glu160, Val198 and Asn212,
Gly36, Thr103, Glu160, Val198 and Ala/Gly232, Gly36, Thr103, Glu160, Val198 and Phe277,
Gly36, Thr103, Glu160, Asn212 and Ala/Gly232,
Gly36, Thr103, Glu160, Asn212 and Phe277,
Gly36, Thr103, Glu160, Ala/Gly232 and Phe277,
Gly36, Thr103, Val198, Asn212 and Ala/Gly232,
Gly36, Thr103, Val198, Asn212 and Phe277,
Gly36, Thr103, Val198, Ala/Gly232 and Phe277,
Gly36, Thr103, Asn212, Ala/Gly232 and Phe277,
Gly36, Glu160, Val198, Asn212 and Ala/Gly232,
Gly36, Glu160, Val198, Asn212 and Phe277,
Gly36, Glu160, Val198, Ala/Gly232 and Phe277,
Gly36, Glu160, Asn212, Ala/Gly232 and Phe277,
Gly36, Val198, Asn212, Ala/Gly232 and Phe277,
Ala95, Thr103, Glu160, Val198 and Asn212,
Ala95, Thr103, Glu160, Val198 and Ala/Gly232,
Ala95, Thr103, Glu160, Val198 and Phe277,
Ala95, Thr103, Glu160, Asn212 and Ala/Gly232,
Ala95, Thr103, Glu160, Asn212 and Phe277,
Ala95, Thr103, Glu160, Ala/Gly232 and Phe277,
Ala95, Thr103, Val198, Asn212 and Ala/Gly232,
Ala95, Thr103, Val198, Asn212 and Phe277,
Ala95, Thr103, Val198, Ala/Gly232 and Phe277,
Ala95, Thr103, Asn212, Ala/Gly232 and Phe277,
Ala95, Glu160, Val198, Asn212 and Ala/Gly232,
Ala95, Glu160, Val198, Asn212 and Phe277,
Ala95, Glu160, Val198, Ala/Gly232 and Phe277,
Ala95, Glu160, Asn212, Ala/Gly232 and Phe277,
Ala95, Val198, Asn212, Ala/Gly232 and Phe277,
Thr103, Glu160, Val198, Asn212 and Ala/Gly232,
Thr103, Glu160, Val198, Asn212 and Phe277,
Thr103, Glu160, Val198, Ala/Gly232 and Phe277,
Thr103, Glu160, Asn212, Ala/Gly232 and Phe277,
Thr103, Val198, Asn212, Ala/Gly232 and Phe277,
Glu160, Val198, Asn212, Ala/Gly232 and Phe277,
Gly36, Ala95, Thr103, Glu160, Val198 and Asn212,
Gly36, Ala95, Thr103, Glu160, Val198 and Ala/Gly232,
Gly36, Ala95, Thr103, Glu160, Val198 and Phe277,
Gly36, Ala95, Thr103, Glu160, Asn212 and Ala/Gly232,
Gly36, Ala95, Thr103, Glu160, Asn212 and Phe277,
Gly36, Ala95, Thr103, Glu160, Ala/Gly232 and Phe277,
Gly36, Ala95, Thr103, Val198, Asn212 and Ala/Gly232,
Gly36, Ala95, Thr103, Val198, Asn212 and Phe277,
Gly36, Ala95, Thr103, Val198, Ala/Gly232 and Phe277,
Gly36, Ala95, Thr103, Asn212, Ala/Gly232 and Phe277,
Gly36, Ala95, Glu160, Val198, Asn212 and Ala/Gly232,
Gly36, Ala95, Glu160, Val198, Asn212 and Phe277,
Gly36, Ala95, Glu160, Val198, Ala/Gly232 and Phe277,
Gly36, Ala95, Glu160, Asn212, Ala/Gly232 and Phe277,
Gly36, Ala95, Val198, Asn212, Ala/Gly232 and Phe277,
Gly36, Thr103, Glu160, Val198, Asn212 and Ala/Gly232,
Gly36, Thr103, Glu160, Val198, Asn212 and Phe277,
Gly36, Thr103, Glu160, Val198, Ala/Gly232 and Phe277,
Gly36, Thr103, Glu160, Asn212, Ala/Gly232 and Phe277,
Gly36, Thr103, Val198, Asn212, Ala/Gly232 and Phe277,
Gly36, Glu160, Val198, Asn212, Ala/Gly232 and Phe277,
Ala95, Thr103, Glu160, Val198, Asn212 and Ala/Gly232,
Ala95, Thr103, Glu160, Val198, Asn212 and Phe277,
Ala95, Thr103, Glu160, Val198, Ala/Gly232 and Phe277,
Ala95, Thr103, Glu160, Asn212, Ala/Gly232 and Phe277,
Ala95, Thr103, Val198, Asn212, Ala/Gly232 and Phe277,
Ala95, Glu160, Val198, Asn212, Ala/Gly232 and Phe277,
Thr103, Glu160, Val198, Asn212, Ala/Gly232 and Phe277,
Gly36, Ala95, Thr103, Glu160, Val198, Asn212 and Ala/Gly232,
Gly36, Ala95, Thr103, Glu160, Val198, Asn212 and Phe277,
Gly36, Ala95, Thr103, Glu160, Val198, Ala/Gly232 and Phe277,
Gly36, Ala95, Thr103, Glu160, Asn212, Ala/Gly232 and Phe277,
Gly36, Ala95, Thr103, Val198, Asn212, Ala/Gly232 and Phe277,
Gly36, Ala95, Glu160, Val198, Asn212, Ala/Gly232 and Phe277,
Gly36, Thr103, Glu160, Val198, Asn212, Ala/Gly232 and Phe277,
Ala95, Thr103, Glu160, Val198, Asn212, Ala/Gly232 and Phe277, or
Gly36, Ala95, Thr103, Glu160, Val198, Asn212, Ala/Gly232 and Phe277.

With respect to the variants it is emphasized that the variants of the amino acid sequence of SEQ ID NO: 1 or 2 according to the present disclosure are functionally active variants. A functionally active variant is a variant that maintains its biological function, e.g., enzymatic activity of a lactate oxidase. Typically, maintenance of biological function is defined as having at least 10%, 20%, 30% or 50%, or at least 60%, more typically at least 70%, 80% or 90%, still more typically 95% or more of the activity of the lactate oxidase of SEQ ID NO: 1 or 2. The biological activity may be determined as known to the skilled person, for example as described in Examples 1 and 2.

In accordance with the present disclosure, the mutant lactate oxidase having increased stability comprises an amino acid sequence that is at least 90% identical to the amino acid sequence of SEQ ID NO: 1 or 2, or a functionally active variant thereof; and has an amino acid substitution at the position corresponding to position Tyr191 of SEQ ID NO: 1 or 2. This means that the mutant lactate oxidase may comprise one or more additional elements in addition to the amino acid as specified above. The element(s) may be a further protein component or non-protein component. In the case of a protein component, the mutant lactate oxidase may be a fusion protein, e.g., having a marker to be used for the isolation, purification or identification of the protein. Further examples of components include linkers (e.g., in order to couple the enzyme to a support), signal sequences (in order to direct the protein to a target) etc. In one alternative, the mutant lactate oxidase may consist of the amino acid sequence as specified above.

In a typical embodiment, the mutant lactate oxidase is characterized in that tyrosine at position 191 is substituted with an essentially non-polar amino acid particularly wherein the amino acid substitution at position 191 is selected from the group consisting of Tyr191Phe, Tyr191Leu, Tyr19Ile, Tyr191Met, and Tyr191Trp, typically the amino acid substitution is Tyr191Phe or Tyr191Leu, more typically Tyr191Phe. As detailed herein, it has been shown that the substitution of Tyr (having a polar OH group) at position 191 with a non-polar amino acid (such as phenylalanine or leucine) increases the stability of the lactate oxidase relative to the wild-type (see Examples). Accordingly, such substitutions are typical. Examples of amino acids with non-polar side groups are glycine, alanine, valine, leucine, isoleucine, and proline. Amino acids having side groups with rather low polarity include methionine and tryptophane, due to the high similarity to phenylalanine and leucine (Met and Tyr would be regarded as conservative amino acid substitutions of Phe or Leu; see above list).

In another typical embodiment of the present disclosure, the mutant lactate oxidase is characterized in that the at least one further amino acid substitution is selected from the group consisting of Gly36Ser, Ala95Gly, Thr103Ser, Glu160Gly, Val198Ile, Asn212Asp, Ala/Gly232Ser, and Phe277Tyr of SEQ ID NO: 1 or 2, particularly when the mutation on position 191 is Tyr191Phe, Tyr191Leu, Tyr191Ile, Tyr191Met, and Tyr191Trp, typically the amino acid substitution is Tyr191Phe or Tyr191Leu, more typically Tyr191Phe. Substitutions of Gly36Ser, Thr103Ser, Glu160Gly, Val198Ile, Asn212Asp, Ala/Gly232Ser, and Phe277Tyr have been shown to confer increased thermal stability to mutant lactate oxidases. Accordingly, those substitutions are typical.

In still another embodiment of the present disclosure, the mutant lactate oxidase is characterized in that the at least one further amino acid substitution is Ala95, typically Ala95Gly. Substitution of Ala95Gly has been shown to improve substrate specificity (see Example 2). Accordingly, Ala at position 95 is typically substituted with Gly.

In accordance with the present disclosure, the mutant lactate oxidase exhibits increased stability. In a typical embodiment of the present disclosure the mutant lactate oxidase has an at least 1.5-fold increased stability relative to the corresponding wild type enzyme, typically an at least 2-fold increased stability, typically an at least 2.5-fold increased stability, more typically an at least 3-fold increased stability. A suitable method for the determination of increased stability is detailed in the Examples. Stability can be determined in buffered solutions of 20 mM HEPES, pH 8.1, 150 mM NaCl, 20 mM NaHCO$_3$ and 0.02-1 mg/ml of lactate oxidase.

In still another embodiment of the present disclosure, the mutant lactate oxidase is characterized in that the mutant lactate oxidase has an at least 2-fold increased selectivity for lactate compared to glycolate relative to the corresponding wild type enzyme, typically an at least 2.5-fold increased selectivity, typically an at least 3-fold increased selectivity, more typically an at least 3.5-fold increased selectivity, and even more typically an at least 4-fold increased selectivity, particularly if the mutant lactate oxidase comprises an amino acid substitution at position A95, particularly Ala95Gly. A suitable method for the determination of increased selectivity is detailed in the Examples.

In a further aspect, the present disclosure relates to a nucleic acid encoding the mutant lactate oxidase also disclosed herein.

The term "nucleic acid" as used herein generally relates to any nucleotide molecule which encodes the mutant lactate oxidase of the present disclosure and which may be of variable length. Examples of a nucleic acid of the disclosure include, but are not limited to, plasmids, vectors, or any kind of DNA and/or RNA fragment(s) which can be isolated by standard molecular biology procedures, including, e.g., ion-exchange chromatography. A nucleic acid of the disclosure may be used for transfection or transduction of a particular cell or organism.

Nucleic acid molecule of the present disclosure may be in the form of RNA, such as mRNA or cRNA, or in the form of DNA, including, for instance, cDNA and genomic DNA, e.g., obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand. Nucleic acid molecule as used herein also refers to, among other, single- and double-stranded DNA or RNA, RNA that is a mixture of single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, nucleic acid molecule as used herein refers to triple-stranded regions comprising RNA or DNA or both RNA and DNA.

Additionally, the nucleic acid may contain one or more modified bases. Such nucleic acids may also contain modifications, e.g., in the ribose-phosphate backbone, to increase stability and half-life of such molecules in physiological environments. Thus, DNAs or RNAs with backbones modified for stability or for other reasons are "nucleic acid molecule" as that feature is intended herein. Moreover, DNAs or RNAs comprising unusual bases, such as inosine, or modified bases, such as tritylated bases, to name just two examples, are nucleic acid molecule within the context of the present disclosure. It will be appreciated that a great variety of modifications have been made to DNA and RNA that serve many useful purposes known to those of skill in the art. The term nucleic acid molecule as it is employed herein embraces such chemically, enzymatically or metabolically modified forms of nucleic acid molecule, as well as the chemical forms of DNA and RNA characteristic of viruses and cells, including simple and complex cells, inter alia.

Furthermore, the nucleic acid molecule encoding the mutant lactate oxidase of the present disclosure can be functionally linked, using standard techniques such as standard cloning techniques, to any desired regulatory sequence, leader sequence, heterologous marker sequence or a heterologous coding sequence to create a fusion protein.

The nucleic acid of the present disclosure may be originally formed in vitro or in a cell in culture, in general, by the manipulation of nucleic acids by endonucleases and/or exonucleases and/or polymerases and/or ligases and/or recombinases or other methods known to the skilled practitioner to produce the nucleic acids.

In a further aspect, the present disclosure relates to an expression vector comprising the nucleic acid of the present disclosure, wherein the nucleic acid is operably linked to a promoter sequence capable of promoting the expression of the nucleic acid in a host cell.

As used herein, the term "expression vector" generally refers to any kind of nucleic acid molecule that can be used to express a protein of interest in a cell (see also above details on the nucleic acids of the present disclosure). In particular, the expression vector of the disclosure can be any plasmid or vector known to the person skilled in the art which is suitable for expressing a protein in a particular host cell including, but not limited to, mammalian cells, bacterial cells, and yeast cells. An expression construct of the present disclosure may also be a nucleic acid which encodes a lactate oxidase of the disclosure, and which is used for subsequent cloning into a respective vector to ensure expression. Plasmids and vectors for protein expression are well known in the art, and can be commercially purchased from diverse suppliers including, e.g., Promega (Madison, Wis., USA), Qiagen (Hilden, Germany), Invitrogen (Carlsbad, Calif., USA), or MoBiTec (Germany). Methods of protein expression are well known to the person skilled in the art and are, e.g., described in Sambrook et al., 2000 (Molecular Cloning: A laboratory manual, Third Edition).

The vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. The vector may be used to transduce, transform or infect a cell, thereby causing the cell to express nucleic acids and/or proteins other than those native to the cell. The vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known (see, e.g., Sambrook, et al., supra).

As detailed above, the nucleic acids which encode a mutant lactate oxidase of the disclosure is operably linked to a sequence which is suitable for driving the expression of a protein in a host cell, in order to ensure expression of the protein. However, it is encompassed within the present disclosure that the claimed expression construct may represent an intermediate product, which is subsequently cloned into a suitable expression vector to ensure expression of the protein. The expression vector of the present disclosure may further comprise all kind of nucleic acid sequences, including, but not limited to, polyadenylation signals, splice donor and splice acceptor signals, intervening sequences, transcriptional enhancer sequences, translational enhancer sequences, drug resistance gene(s) or alike. Optionally, the drug resistance gene may be operably linked to an internal ribosome entry site (IRES), which might be either cell cycle-specific or cell cycle-independent.

The term "operably linked" as used herein generally means that the gene elements are arranged as such that they function in concert for their intended purposes, e.g., in that transcription is initiated by the promoter and proceeds through the DNA sequence encoding the protein of the present disclosure. That is, RNA polymerase transcribes the sequence encoding the fusion protein into mRNA, which in then spliced and translated into a protein.

The term "promoter sequence" as used in the context of the present disclosure generally refers to any kind of regulatory DNA sequence operably linked to a downstream coding sequence, wherein said promoter is capable of binding RNA polymerase and initiating transcription of the encoded open reading frame in a cell, thereby driving the expression of said downstream coding sequence. The promoter sequence of the present disclosure can be any kind of promoter sequence known to the person skilled in the art, including, but not limited to, constitutive promoters, inducible promoters, cell cycle-specific promoters, and cell type-specific promoters.

The nucleic acid or expression vector of the present disclosure may be comprised in a host cell. Accordingly, another aspect of the present disclosure relates to a host cell comprising the nucleic acid or expression vector of the present disclosure. A "host cell" of the present disclosure can be any kind of organism suitable for application in recombinant DNA technology, and includes, but is not limited to, all sorts of bacterial and yeast strains which are suitable for expressing one or more recombinant protein(s). Examples of host cells include, for example, various *Bacillus subtilis* or *E. coli* strains. A variety of *E. coli* bacterial host cells are known to a person skilled in the art and include, but are not limited to, strains such as DH5-alpha, HB101, MV1190, JM109, JM101, or XL-1 blue which can be commercially purchased from diverse suppliers including, e.g., Stratagene (CA, USA), Promega (WI, USA) or Qiagen (Hilden, Germany). A particularly suitable host cell is also described in the Examples, namely *E. coli* BL21 Gold cells. *Bacillus subtilis* strains which can be used as a host cell include, e.g., 1012 wild type: leuA8 metB5 trpC2 hsdRM1 and 168 Marburg: trpC2 (Trp-), which are, e.g., commercially available from MoBiTec (Germany).

The cultivation of host cells according to the disclosure is a routine procedure known to the skilled person. That is, a nucleic acid encoding a mutant lactate oxidase of the disclosure can be introduced into a suitable host cell(s) to produce the respective protein by recombinant means. These host cells can be any kind of suitable cells, typically bacterial cells such as *E. coli*, which can be cultivated in culture. At a first step, this approach may include the cloning of the respective gene into a suitable plasmid vector. Plasmid vectors are widely used for gene cloning, and can be easily introduced, i.e., transfected, into bacterial cells which have been made transiently permeable to DNA. After the protein has been expressed in the respective host cell, the cells can be harvested and serve as the starting material for the preparation of a cell extract containing the protein of interest. A cell extract containing the protein of interest is obtained by lysis of the cells. Methods of preparing a cell extract by means of either chemical or mechanical cell lysis are well known to the person skilled in the art, and include, but are not limited to, e.g., hypotonic salt treatment, homogenization, or ultrasonification. An example for a suitable method for the cultivation of a host cell for expressing a mutant lactate oxidase of the disclosure is described in Examples 1 and 2.

Another aspect of the present disclosure relates to a method of determining lactate in a sample, the method comprising:
a) contacting the sample with the mutant lactate oxidase of the present disclosure under conditions conducive to the activity of the lactate oxidase; and
b) determining:
   i) pyruvate and/or $H_2O_2$ produced by the mutant lactate oxidase in the presence of lactate; and/or
   ii) $O_2$, consumed by the mutant lactate oxidase in the presence of lactate, thereby determining lactate.

The above method is based on the fact that lactate oxidase may be used to catalyze the oxidation of L-lactate to pyruvate according to the following scheme:

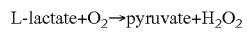

$$\text{L-lactate} + O_2 \rightarrow \text{pyruvate} + H_2O_2$$

In a first step of the method according to an embodiment of the present disclosure, a sample is contacted with the mutant lactate oxidase of the present disclosure. The contacting of the sample with the mutant lactate oxidase can be direct (e.g., in liquid assays) or indirect (e.g., in sensor systems in which only a fraction of the sample (containing the analyte) is contacting the mutant lactate oxidase).

It is evident that the contacting should be carried out under conditions conducive to the activity of the lactate oxidase, i.e., allowing the enzyme to oxidize lactate to pyruvate. The incubation step can vary from about 5 seconds to several hours, typically from about 10 seconds to about 10 minutes. The actual incubation time will depend upon the assay format, volume of solution, concentrations and the like. Usually the assay will be carried out at ambient temperature or a temperature required for other test formats carried out concomitantly (e.g., 25° C. to 38° C.; such as 30° C. or 37° C.), although it can be conducted over a range of temperatures, such as 10° C. to 40° C.

Optionally, the enzyme can be fixed to or immobilized on a support layer prior to the contacting with the sample to facilitate the assay. Examples of support layers include glass or plastic in the form of, for example, a micro-titer plate, a glass microscope slide or cover slip, a stick, a bead, or a micro-bead, membranes (e.g., used in test strips) and layers of biosensors.

The sample may be any sample suspected of containing lactate, including a sample from a subject. The term "sample from a subject" includes all biological fluids, excretions and tissues isolated from any given subject, particularly a human. In the context of the present disclosure such samples include, but are not limited to, blood, blood serum, blood plasma, nipple aspirate, urine, semen, seminal fluid, seminal plasma, prostatic fluid, excreta, tears, saliva, sweat, biopsy, ascites, cerebrospinal fluid, milk, lymph, bronchial and other lavage samples, or tissue extract samples. Typically, the subject is an animal (including human), more typically a mammal, still more typically a human.

Alternatively, samples suspected of containing lactate may be also lactate containing food or beverage samples, like yogurt, kefir, or milk, or a fermentation or cell culture media.

Blood samples are typical test samples for use in the context of the present disclosure. Samples of blood may be drawn from a vein, usually from the inside of the elbow or the back of the hand. Particularly, in infants or young children, a sharp tool called a lancet may be used to puncture the skin and make it bleed. The blood may be collected, e.g., into a pipette, or onto a slide or test strip.

After the contacting step and the oxidation of lactate, if present, pyruvate and/or $H_2O_2$ produced by the mutant lactate oxidase in the presence of lactate and/or $O_2$ consumed are determined, thereby determining lactate in the sample. The amounts of pyruvate and/or $H_2O_2$ produced by the mutant lactate oxidase and the amount of $O_2$ consumed correlates with the amount of lactate present in the sample.

A variety of methods for determining pyruvate, $H_2O_2$ and/or $O_2$ are known in the art and any of these can be used.

Exemplary methods for determining pyruvate include colorimetric methods (e.g., by measuring lactate dehydrogenase-mediated NADH/NAD$^+$ conversion at 340 nm), gas chromatography methods, HPLC analysis, etc. Also methods involving lactate dehydrogenase and decarboxylating pyruvate oxidase are known to the skilled person.

Known methods for the detection of $H_2O_2$ include classical analytic methods such as the $H_2O_2$ mediated conversion of $CrO_3$ to $CrO(O_2)_2$, methods involving iodide and starch, photometric methods (see also below), optical methods (optionally in cuvette or with a sensor often with horseradish peroxidase mediating oxidation of a dye), fluorometric methods such as peroxidase-mediated oxidation of 10-acetyl-3,7-dihydroxyphenoxazine by $H_2O_2$ to resorufin (read out at 590 nm), luminometric methods (e.g., using chemoluminescence of luminol) and amperometric methods, e.g., based on the anodic oxidation of a working electrode (e.g., platinum electrode at 650 mV vs. AgAgC1) by $H_2O_2$, wherein the resulting current is indicative of the amount of $H_2O_2$. In a typical method of the present disclosure, the enzyme peroxidase may be used for the determination of $H_2O_2$.

A particular suitable method for determining $H_2O_2$ is described in the following: For the determination of $H_2O_2$, the enzyme peroxidase may be used. Peroxidase is particularly useful when it is used to generate a colored dye in the presence of using $H_2O_2$. The reaction may be expressed as follows:

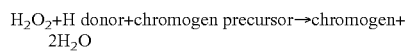

The intensity of the color formed by this reaction is proportional to the L-lactate concentration and may be determined by measuring the increase in absorbance.

Suitable chromogen precursors (and suitable wavelengths for read out) include:

ABTS: 2,2'-azino-di-[3-ethylbenzthiazoine sulfonate(6)] (read out at 410 nm);

4-APP: 4-Aminoantipyrine (read out at 510 nm); and

TMB: 3,3',5,5'-Tetramethylbenzidine (read out at 450 nm).

A variety of peroxidase substrates including chromogen precursors are commercially available, e.g., from Sigma-Aldrich (St. Louis, Mo., USA).

Although there are many suitable chromogenic and luminogenic substrates for peroxidases, there are very few fluorogenic peroxidase substrates used. Fluorogenic peroxidase substrates such as dihydrofluorescein (also known as fluorescein), dihydrorhodamines and dihydroethidium (hydroethidine) are converted to fluorescent products in the presence of the enzyme and hydrogen peroxide. An example of a stable and sensitive fluorogenic substrate is 10-acetyl-3,7-dihydroxyphenoxazine (ADHP).

The peroxidase may be any peroxidase capable of converting the chromogen precursor to the chromogen depending from the presence of $H_2O_2$. One frequently used peroxidase is horseradish peroxidase.

Exemplary methods for determining $O_2$ include gas chromatography, amperometric methods, e.g., with Clark electrode, or fluorometric methods, e.g., involving the $O_2$-caused quenching of fluorescence of particular dyes. Determination of $O_2$ may involve an oxygen optode. An optode or optrode is an optical sensor device that optically measures a specific substance (e.g., $O_2$) usually with the aid of a chemical transducer.

For measuring the oxidation of lactate by lactate oxidase, a mediator may be used instead of $O_2$. If so, the concentration of the mediator rather than $O_2$ may be determined. This is typical for test strip based assays; this technique may be used in order to guarantee independence from the effects of ambient oxygen on the accuracy of the test.

In accordance with the method of an embodiment of the present disclosure, lactate can be determined by determining pyruvate and/or $H_2O_2$ produced and/or $O_2$ consumed by the mutant lactate oxidase in the presence of lactate. The method is designed in a manner that the amount of pyruvate and/or $H_2O_2$ produced by the mutant lactate oxidase is directly proportional to the amount of lactate in the sample and that the amount of $O_2$ consumed is reciprocally proportional to the amount of lactate in the sample. Accordingly, the amount of lactate in the sample can be derived (e.g., calculated) from the amount of pyruvate and/or $H_2O_2$ produced and/or $O_2$ consumed. Typical methods for such calculations include, for example, standard curves, calibration steps, etc.

The method may be used, e.g., as a diagnostic assay. As detailed above, an altered lactate level may be associated with lactic acidosis, i.e., an accumulation of lactic acid/lactate. If the lactate level is changed relative to a control or reference, this may be indicative of lactic acidosis, e.g., due to exercise and/or a disease or metabolic disorder.

In diagnostic methods, the lactate value determined for the sample may be compared to a reference. The reference may be a sample from a healthy subject or it may be a range or value determined from a group of healthy subjects. Alternatively, it may be a known reference value. For human blood samples and human plasma samples, lactate concentrations in the range of from 0.5-2.2 mmol/L (typically 1.0-1.8 mmol/l) and 0.9-1.7 mmol/L, respectively, are usually regarded as normal. If lactate determination is used for monitoring training, the blood lactate concentration during endurance training should be up to 3-4 mmol/L. During longer training sessions (more than 45 min), a lower lactate concentration is typical (around or less than 2 mmol/L). Generally, during endurance training lactate concentrations greater than 4 mmol/L, are to be avoided.

The person skilled in the art knows statistical procedures necessary to assess whether two values are significantly different from each other. Such methods include, for example, the Student's t-test or chi-square tests. Furthermore, the skilled person knows how to select a suitable control.

The method can be carried out in a so-called liquid or wet test, for example in a cuvette, or as a so-called dry test on an appropriate reagent carrier, the necessary test reagents thereby being present in or on a solid carrier, which is typically an absorbent or swellable material.

In a typical embodiment the determination of $H_2O_2$ may be performed by conversion into a chromogen, particularly by peroxidase-mediated conversion, as described above.

Alternatively or additionally, the mutant lactate oxidase may be part of a sensor, a test strip, a test element, a test strip device or a liquid test.

A sensor is an entity that measures a physical/chemical quantity and converts it into a signal which can be read by an observer or by an instrument. In the present disclosure, the mutant lactate oxidase may be part of a sensor, wherein the sensor converts lactate into a signal such as a change in color or a value displayed, e.g., on a display or monitor.

In one embodiment, the lactate sensor may be composed of the mutant lactate oxidase and an amperometric device to determine the level hydrogen peroxide associated with a sample. Also, a microdialysis system coupled with an electrochemical flow cell could be used to continuously monitor the level of lactate in a sample or subject. The working electrode of the flow cell could be prepared with the mutant lactate oxidase immobilized in a redox polymer film on the electrode surface. Coupling an electrochemical lactate sensor directly with microdialysis eliminates the need to transfer sample aliquots to a liquid chromatography system with a post-column oxidase enzyme reactor. Lactate in the dialysate from the microdialysis probe can be selectively detected at the enzyme electrode without any significant interference from other oxidizable species. Furthermore, enzyme-coupled biosensors have been described in the art. In accordance with this, mutant lactate oxidase may be coupled to a surface (e.g., by printing a mutant lactate oxidase/graphite mixture onto electroplated graphite pads or by adsorption or immobilization of the mutant lactate oxidase on carbon particles, platinized carbon particles, carbon/manganese dioxide particles, glassy carbon, or mixing it with carbon paste electrodes etc.) in order to detect hydrogen peroxide electrochemically.

A test strip or a test element is an analytic or diagnostic device used to determine presence and/or quantity of a target substance within a sample. A standard test strip may comprise one or more different reaction zones or pads comprising reagents which react (e.g., change color) when contacted (e.g., immersed in, and then removed from) a sample. Test strips are known in many embodiments, for example from EP Pat. No. 262445 and U.S. Pat. No. 4,816,224. A commercially available example of a lactate test based on test strip technology is the BM Lactate test for the Accutrend meter of Roche Diagnostics (Mannheim, Germany). It is commonly known that one or more reagents (e.g., enzymes) needed for carrying out the determination methods are present on or in solid carrier layers. As carrier layers, there are absorbent and/or swellable materials which are wetted by the sample liquid to be analyzed. Examples include gelatine, cellulose and synthetic fiber fleece layers.

The mutant lactate oxidase may also be part of a liquid test. A liquid test is a test wherein test components react in a liquid medium. A commercially available example of a liquid lactate test is the lactate test for the cobas c 111 analyzer of Roche Diagnostics (Mannheim, Germany). Usually in the field of laboratory analytics, the liquid reagents are water based, e.g., a buffered salt solution is used in order to provide an environment conducive to the activity of enzyme(s) involved. The liquid is usually adapted to the specific intended use. For carrying out a liquid test, all test components are solved in a liquid and combined (or vice versa). Typical containments for carrying out such tests include vials, multi-well plates, cuvettes, vessels, reagent cups, tubes, etc.

In one embodiment of the present disclosure, the mutant lactate oxidase of the present disclosure may be immobilized. Typical methods of immobilization include covalent binding, e.g., to a membrane, encapsulation in a polymer, cross-linking to a supporting matrix or immobilization in a sol-gel matrix (e.g., glasses such as silicate glasses) or adsorption on porous substrates. Suitable methods for immobilizing enzymes such as lactate oxidase are known in the art (see, e.g., Lillis, et al., 2000, *Sensors and Actuators* B 68: 109-114).

Another aspect of the present disclosure relates to the use of a mutant lactate oxidase of the present disclosure for determining lactate. Suitable methods involving the use of the mutant lactate oxidase of the present disclosure for determining lactate are described above.

In another aspect, the present disclosure provides a device for determining lactate in a sample, the device comprising a mutant lactate oxidase according to the present disclosure and optionally a further component, such as other reagents, required for said determining.

The mutant lactate oxidase of the present disclosure may be part of a device for determining lactate in a sample. The device may be any device suitable for this purpose. The device may be a machine or tool which can be used for determining lactate. Typically, the device is a sensor, i.e., an electrochemical sensor, or a test strip. Exemplary devices are described above and in the following:

The device may be a sensor, e.g., a biosensor, which is an analytical device for the detection of an analyte that combines a biological component (here the mutant lactate oxidase according to the present disclosure) with a detector component, particularly a physicochemical detector component.

Biosensors are particularly useful to determine the concentration of various analytes (including lactate) from biological samples, particularly from blood. Exemplary biosensors based on an electrochemical test strip format are described in U.S. Pat. Nos. 5,413,690; 5,762,770 and 5,997,817, each of which is incorporated herein in its entirety as if each were incorporated individually.

In the (bio)sensor of the present disclosure, lactate and $O_2$ are converted into pyruvate and $H_2O_2$ in the presence of the mutant lactate oxidase and the increase in any of the products or the decrease in any of the substrates may be monitored by the transducer or detector element.

Particularly, lactate sensors have been combined with other sensors, e.g., for determining glucose, cholesterol, triglycerides, urea, blood gases or electrolytes, etc. Evidently, the mutant lactate oxidase of the present disclosure could also be used in these multi-analyte devices.

As detailed above, the sensor can be an electrochemical sensor. An electrochemical sensor is based on the translation of a chemical signal (here presence of lactate) into an electrical signal (e.g., current). A suitable electrode can measure the lactate oxidase-mediated formation of hydrogen peroxide, as an electrical signal. The signal is produced following the transfer of electrons from the hydrogen peroxide to the electrode, and under suitable conditions the enzyme-catalyzed flow of current is proportional to the lactate concentration.

Another commercially available example of a lactate biosensor is the multi-use lactate sensor of the cobas b 123 analyzer of Roche Diagnostics (Mannheim, Germany). For multiple-use biosensors, two main groups of biosensors have been commercialized, membrane-based sensors (e.g., from YSI, Eppendorf, Nova Biomedical and Radiometer), as well as thick film biosensors from Bayer or Roche.

In one embodiment of the present disclosure, the sensor provides an electrochemical sensor including an electrically nonconductive substrate, a working electrode, and a semi-permeable membrane covering the working electrode, which permits lactate and oxygen to pass through to the electrode. The working electrode includes an electrically conductive material adhered to a portion of the substrate and a catalytically active quantity of the lactate oxidase. The sensor may further include a counter electrode having a second electrically conductive material adhered to a second portion of the nonconductive substrate. The semi-permeable membrane can be formed from cellulose acetate, polyurethane, silicone compounds, and other materials known in the art. In another embodiment of the present disclosure, the electrochemical sensor may further include a reference electrode.

In another exemplary electrochemical sensor, the mutant lactate oxidase is immobilized in an enzyme layer (e.g., via a self-cross linking acrylate polymer). The translation of the chemical signal into an electronic signal is achieved by a manganese dioxide layer responding to $H_2O_2$. Further components are a reference electrode in addition to the working electrode. Exemplary sensors are also described in Schaffar et al., 1999, Clinical Chemistry 45(9): 1678-1679.

The device of the present disclosure may comprise—in addition to the mutant lactate oxidase—one or more further component(s), such as other reagents, required for or helpful in said determining. The components may be any of these described in the context of the methods and devices of the present disclosure. Additionally, this may include an instruction manual, a lancet device, a capillary pipette, a further enzyme (such as peroxidise), a substrate (such as a chromogen precursor) and/or a lactate control solution, etc.

Still in another aspect, the present disclosure provides a kit for determining lactate comprising a mutant lactate oxidase according to the present disclosure and at least one further agent required for said determining.

As a matter of convenience, the mutant lactate oxidase according to the present disclosure can be provided in a kit, such as a packaged combination of reagents in predetermined amounts with instructions for performing a (diagnostic) assay. Where necessary, the kit will include substrates, precursors of chromophores, further enzymes (such as peroxidase) and cofactors required by the enzyme. Other additives may be included in the kit such as stabilizers, buffers (e.g., a block buffer, lysis buffer or dilution buffer) and the like. The relative amounts of the various reagents provided in the kit may be varied widely, for example, to provide for concentrations in solution of the reagents which substantially optimize the sensitivity of the assay. The reagents may be provided as dry powders, usually lyophilized, including excipients, for example, which on dissolution will provide a reagent solution having the appropriate concentration.

The present disclosure is not limited to the particular methodology, protocols, and reagents described herein because they may vary. Further, the terminology used herein is for the purpose of describing particular embodiments only and is not intended to limit the scope of the present disclosure. As used herein and in the appended claims, the singular forms "a", "an", and "the" include plural reference unless the context clearly dictates otherwise. Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the disclosure. Although any methods and materials similar or equivalent to those described herein can be used in the practice of the present disclosure, the typical methods, and materials are described herein.

In order that the embodiments of the disclosure may be more readily understood, reference is made to the following examples, which are intended to illustrate but not to limit the scope thereof.

EXAMPLES

Example 1

Lactate Oxidase with Increased Stability

1. Materials and Methods
Genetics

A plasmid containing wild type lactate oxidase (according to SEQ ID NO: 1) was used as starting material. The plasmid was a p-LO1 plasmid having a tac promoter. Accordingly, the protein expression may be induced by IPTG (isopropyl β-D-1-thiogalactopyranoside). Furthermore, the plasmid has an ampicillin resistance gene.

In order to substitute amino acid tyrosine at position 191 with phenylalanine, the primers in SEQ ID NO: 3 and SEQ ID NO: 4 were used.

In order to substitute amino acid tyrosine at position 191 with leucine, the primers in SEQ ID NO: 5 and SEQ ID NO: 6 were used.

The modified nucleo-bases are shown in bold letters. The codon coding for the substituted amino acid is identified by underlining, and the recognition sequence for restriction enzyme PvuI is shown in italic font. A two-stage PCR was carried out according to the protocol published by Wang and co-workers (Wang, et al., *BioTechniques,* 1999, 26:680-682). Thereafter, the PCR product was incubated at 37° C. with DpnI for 30 minutes and then transformed in *E. coli* BL21 gold cells. The cells were streaked out on LB ampicillin plates and on the following day plasmid DNA was isolated therefrom. Before mutation was confirmed by sequencing, plasmids were selected using a PvuI cleavage-based assay.

Cultivation and Purification

Cells as described above were cultivated in LB medium with ampicillin (100 mg/l) at 30° C. and expression with IPTG (250 µM) was induced after having reached an optical density of 0.8 at 595 nm. After a 4-hour expression at 30° C., cells were harvested, resuspended in 50 mM potassium phosphate buffer (pH 7.0; referred to as KPP) and dissociated using a French press. Cellular debris was removed by ultracentrifugation, and the crude extract was used for protein purification.

For this, a portion of the *E. coli* proteins was precipitated with 1.5 M $(NH_4)_2SO_4$ while stirring. The supernatant was transferred to a HiTrap Phenyl FF hydrophobic interaction chromatography (HIC) column (inner diameter: 16 mm; volume: 64 ml; protein: 30 mg). Thereafter, lactate oxidase was eluted using a gradient of 50 mM KPP, pH 7.0, 1.5 M $(NH_4)_2SO_4$ (Buffer A) to 50 mM KPP, pH 7.0 (Buffer B) (flow rate 2.5 ml/min). A lactate oxidase peak could be identified at 70% Buffer B. After buffer substitution to Buffer B, 10 mg of protein were transferred to an anion exchange column (MonoQ) (inner diameter: 5 mm; column volume: 5 ml). Elution was carried out stepwise at a flow rate of 1.5 ml/min using Buffer B plus 1 M KCl (Buffer C). Lactate oxidase eluted at 28% Buffer C. After buffer substitution to Buffer B aliquots of 100 μl were taken and frozen.

Determination of Activity

Activity was determined using a protocol of Sigma Aldrich, wherein the concentration of the L-lactate stock solution was reduced by factor 10 to 50 mM for stability assessment and the reaction volume was reduced by a factor 2.

The Protocol of Sigma Aldrich is as Follows:

In the presence of $H_2O_2$, peroxidase mediates the reaction of aminoantipyrine (4-AAP) and N,N-dimethylaniline (DMA) to obtain a quinonediimine dye. The test is carried out at the following conditions: T=37° C., pH=6.5, A565 nm, Light path=1 cm using the following reagents:

A. 200 mM 3,3-Dimethylglutaric Acid-NaOH Buffer, pH 6.5 at 37° C. (DMGA) (Prepare 5 ml in deionized water using 3,3-Dimethylglutaric Acid, Sigma Prod. No. D-4379. adjust to pH 6.5 at 37° C. with 1 M NaOH.)

B. 15 mM 4-Aminoantipyrine Solution (4-AAP) (Prepare 1 ml in deionized water using 4-Aminoantipyrine, Free Base, Sigma Prod. No. A-4382.)

C. 500 mM L(+)Lactic Acid Solution, pH 6.5 at 37° C. (Lactic Acid) (Prepare 1 ml in deionized water using L(+)Lactic Acid, Free Acid, Sigma Prod. No. L-1750. Adjust to pH 6.5 with 1 M NaOH.)

D. Peroxidase Enzyme Solution (POD) (Immediately before use, prepare a solution containing 50 Purpurogallin units/ml of Peroxidase Type II from Horseradish, Sigma Prod. No. P-8250, in cold deionized water.)

E. 10 mM Potassium Phosphate Buffer with 0.010 mM Flavin Adenine Dinucleotide (FAD), pH 7.0 at 37° C. (Enzyme Diluent) (Prepare 50 ml in deionized water using Potassium Phosphate, Monobasic, Anhydrous, Sigma Prod. No. P-5379, and Flavin Adenine Dinucleotide, Disodium Salt, Sigma Prod. No. F-6625. Adjust to pH 7.0 at 37° C. with 1 M NaOH. PREPARE FRESH.)

F. 0.2% (v/v) N,N-Dimethylaniline Solution (DMA) (Prepare 10 ml in deionized water using N,N-Dimethylaniline, Sigma Prod. No. D-8509.)

G. 0.25% (w/v) Dodecylbenzenesulfonic Acid Solution (DBS) (Prepare 5 ml in deionized water using Dodecylbenzenesulfonic Acid, Sodium Salt, Sigma Prod. No. D-2525.)

H. Lactate Oxidase Enzyme Solution (LOX) (Immediately before use, prepare a solution containing 0.1-0.2 units/ml of Lactate Oxidase in cold Reagent E.)

The assay procedure is as follows:

Prepare a reaction cocktail by pipetting (in milliliters) the following reagents into a suitable container: Reagent A (DMGA) 2.00, Reagent D (POD) 1.00, Reagent B (4-AAP) 1.00, Reagent C (Lactic Acid) 1.00, Deionized Water 3.00. Mix by inversion and equilibrate to 37° C. Pipette (in milliliters) the following reagents into a suitable cuvette: Reaction Cocktail 0.80, Reagent G (DMA) 0.20. Mix by inversion and equilibrate to 37° C. Then add: Reagent I (LOX) 0.020 for test samples or Reagent E (Enzyme Diluent) for blank. Immediately mix by inversion and incubate at 37° C. for exactly 10 minutes. Then add: Reagent H (DBS) 2.00. Mix by inversion and record the A565 nm for both the Test and Blank using a suitable spectrophotometer.

The activity (U/mg enzyme) is to be calculated as follows:

$$\text{Activity [Units/mg enzyme]} = \frac{(A565 \text{ nm Test} - A565 \text{ nm Blank})(3.02)(df)}{(35.33)(0.5)(10)(0.02)}$$

wherein
3.02=Total volume of assay
df=Dilution factor
35.33=Millimolar extinction coefficient of Quinonediimine dye at 565 nm.
0.5=Conversion factor based on one mole of $H_2O_2$ produces half a mole of Quinonediimine dye
10=Time of assay (in minutes) as per unit definition
0.02=Volume (in milliliter) of enzyme used In a 1.02 ml reaction mix, the final concentrations are 39 mM 3,3 dimethylglutaric acid, 5 units peroxidase, 1.5 mM 4-aminoantipyrine, 49 mM L(+)lactic acid, 0.04% (v/v), N,N-dimethylaniline, 0.20 mM potassium phosphate, 0.20 μm FAD and 0.002-0.004 unit lactate oxidase.

One unit will oxidize 1.0 μmole of L-lactate to pyruvate and $H_2O_2$ per minute at pH 6.5 at 37° C.

Data obtained were fitted according to the following equations:

No substrate inhibition: $v=v_{max}*[S]/(K_m+[S])$ (equation 1)

Substrate inhibition: $v=v_{max}*[S]/(K_m+[S]*(1+[S]/[I]))$ (equation 2)

v=reaction rate, $v_{max}$=maximum rate, [S]=concentration of substrate, $K_m$=Michaelis constant, [I]=concentration of inhibitor.

Stability Determination

In order to better determine inactivation, accelerated stability determinations were carried out using the following conditions: 20 mM HEPES, pH 8.1, 150 mM NaCl, 20 mM $NaHCO_3$ and 0.05 mg/ml lactate oxidase. Samples were centrifuged before determination of activity and incubation was carried out at 37° C.

2. Results

Mutant lactate oxidases having tyrosine at position 191 substituted with phenylalanine (referred to as Tyr191Phe) or with leucine (referred to as Try191Leu) were expressed and purified as described above. Purity was confirmed using SDS gel chromatography.

For Tyr191Phe, the specific activity of the mutant could be determined as 23 U/mg. In comparison to the wild type, the activity was reduced eight-fold. The Michaelis or affinity constant $K_m$ was 0.017 mM for mutant Tyr191Phe and was significantly lower than that of the wild type (0.897 mM). Furthermore, the mutant showed also significant substrate inhibition (I=48.4 mM in comparison to the wild type as shown in FIG. 1A).

Stability of mutant Tyr191Phe was determined for a period of three weeks, whereby samples were taken regularly and activity of the samples was determined. The results were normalized with respect to t=0. In order to better determine inactivation, accelerated stability determination (as described above) was carried out, whereby inactivation was increased by change of ambient conditions. With the conditions chosen, wild type (control) had a half-life of 4.5 days. In contrast thereto, mutant Tyr191Phe showed significantly higher stability under these conditions and 50% of the original activity was reached after 9.8 days, which is equivalent to a 2.2-fold increase in stability.

For the Try191Leu mutant the specific activity of the mutant could be determined to be 16 U/mg. In comparison to the wild type, the activity of this mutant was reduced twelve fold. The Michaelis or affinity constant $K_m$ for this enzyme was 1.065 mM for mutant Try191Leu and was almost the same as that of the wild type (0.897 mM). The mutant Try191Leu showed no significant substrate inhibition.

The stability of mutant Try191Leu was determined for a period of three weeks, whereby samples were taken regularly and activity of the samples was determined. The results were normalized with respect to t=0. In order to better determine inactivation, accelerated stability determination (as described above) was carried out, whereby inactivation was increased by change of ambient conditions. With the conditions chosen, wild type (control) had a half-life of 3.8 days. In contrast thereto, mutant Try191Leu showed significantly higher stability under these conditions and 50% of the original activity was reached after 7.4 days, which is equivalent to a 1.6-fold increase in stability.

It can be concluded that mutants Tyr191Phe and Try191Leu have significantly improved stabilities in comparison to the wild-type, and can drastically increase lifetime of sensors and tests.

Example 2

Lactate Oxidase with Improved Selectivity

1. Materials and Methods
Genetics

The plasmid containing wild type lactate oxidase as described in Example 1 was used as starting material.

In order to substitute amino acid alanine at position 95 with glycine, the primers in SEQ ID NO: 7 and SEQ ID NO: 8 were used. The modified nucleobases are shown in bold letter. The codon coding for the substituted amino acid is identified by underlining, and the recognition sequence for restriction enzyme NcoI is shown in italic font. A two-stage PCR was carried out according to the protocol published by Wang and co-workers (Wang, et al., supra). Thereafter, the PCR product was incubated at 37° C. with DpnI for 30 minutes and then transformed in *E. coli* BL21 gold cells. The cells were streaked out on LB ampicillin plates and on the following day plasmid DNA was isolated therefrom. Before mutation was confirmed by sequencing, plasmids were selected using an NcoI cleavage-based assay.

Cultivation and Purification

Cells as described above were cultivated in LB medium with ampicillin (100 mg/l) at 30° C. and expression with IPTG (250 μM) was induced after having reached an optical density of 0.8 at 595 nm. After a 4-hour expression at 30° C., cells were harvested, resuspended in 50 mM potassium phosphate buffer (pH 7.0; referred to as KPP) and dissociated using a French press. Cellular debris was removed by ultracentrifugation, and the crude extract was used for protein purification.

For this, a portion of the *E. coli* proteins was precipitated with 1.5 M $(NH_4)_2SO_4$ while stirring on ice. The supernatant was transferred to a High Trap Phenyl FF hydrophobic interaction chromatography (HIC) column (inner diameter: 16 mm; volume: 64 ml; protein: 30 mg). Thereafter, lactate oxidase was eluted using a gradient of 50 mM KPP, pH 7.0, 1.5 M $(NH_4)_2SO_4$ (Buffer A) to 50 mM KPP, pH 7.0 (Buffer B) (flow rate 2.5 ml/min). A lactate oxidase peak could be identified at 70% Buffer B. After buffer substitution to Buffer B, 10 mg. of the protein were transferred to an anion exchange column (MonoQ) (inner diameter: 5 mm; column volume: 5 ml). Elution was carried out stepwise at a flow rate of 1.5 ml/min using Buffer B plus 1 M KCl (Buffer C). Lactate oxidase eluted at 28% Buffer C. After buffer exchange to Buffer B aliquots of 100 μl were taken and frozen.

Determination of Activity

Activity was determined using a protocol of Sigma Aldrich at 37° C. (see Example 1).

Selectivity for L-lactate ($R_{sel}$) was calculated by determining the ratio of the respective catalytic efficiencies $K_{cat}/K_m$ for lactate (lac) relative to glycolate (glyc) ($R_{sel}=[(K_{cat,lac}/K_{m,lac})/(K_{cat,glyc}/K_{m,glyc})]$, wherein $K_{cat}$ (turnover number) is the maximum number of molecules of substrate that an enzyme can convert to product per unit of time. Data obtained were fitted according to the following equation:

$$\text{No substrate inhibition: } v = v_{max} * [S]/(K_m + [S]) \qquad \text{(equation 1)}$$

v=reaction rate, $v_{max}$=maximum rate, [S]=concentration of substrate, $K_m$=Michaelis constant When measuring substrate inhibition, the value $K_{cat}/K_m$ was extrapolated from the linear region at low substrate concentration.

Stability Determination

In order to better determine inactivation, accelerated stability determinations were carried out using the following conditions: 20 mM HEPES, pH 8.1, 150 mM NaCl, 20 mM $NaHCO_3$ and 0.05 mg/ml lactate oxidase. Samples were centrifuged before determination of activity and incubation was carried out at 37° C.

2. Results

In this example, L-lactate is the preferred substrate of the lactate oxidase. Using the above purification protocol an activity of 44.5 $sec^{-1}$ was determined. The $K_m$ value was determined as 0.23 mM resulting in a catalytic efficiency of 193.4 $sec^{-1}$ $mM^{-1}$. The catalytic efficiency for glycolate was measured under identical conditions. Due to the high substrate inhibition observed, the linear region at low substrate concentration was used for the determination of $K_{cm}/K_m$ (2.4 $sec^{-1}$ $mM^{-1}$). In accordance with the above efficiency, the selectivity $R_{sel}$ of lactate was 80.4.

Mutant Ala95Gly was prepared as described above and purified to homogeneity. Homogeneity was confirmed by SDS gel electrophoresis. The purified enzyme was characterized as the wild-type enzyme. The $K_m$ value for lactate (0.63 mM) increased by factor 3 relative to the wild-type, resulting in a loss of activity for lactate (21.5 $sec^{-1}$) as a substrate. The smaller substrate glycolate again showed strong substrate inhibition. Using the above method, a catalytic efficiency $K_{cat}/K_m$ of 0.089 $sec^{-1}$ $mM^{-1}$ was determined. The combination of effects results in an altered selectivity (determined by comparing catalytic efficiency) which can be determined as $R_{sel}$=384 for mutant Ala95Gly. In comparison to the wild type, the selectivity is increased by factor 4.8 (see also Table 1).

TABLE 1

Kinetic constants of wild-type lactate oxidase (WT) and mutant Ala95Gly

| | L lactate | | | glycolate | | | | |
|---|---|---|---|---|---|---|---|---|
| | $K_m$ [mM] | $K_{cat}$ [s$^{-1}$] | $K_{cat}/K_m$ [s$^{-1}$mM$^{-1}$] | $K_m$ [mM] | $K_{cat}$ [s$^{-1}$] | $K_{cat}/K_m$ [s$^{-1}$mM$^{-1}$] | $R_{Sel}$ | $R_{Sel}$(Ala95Gly)/ $R_{Sel}$(WT) |
| WT | 0.23 | 44.5 | 193.4 | | | 2.4 | 80.6 | 4.8 |
| Ala95Gly | 0.63 | 21.5 | 34.2 | | | 0.089 | 384 | |

* Due to the strong substrate inhibition, no $K_m$ and $K_{cat}$ values could be calculated for glycolate. As described also within the text of this application, the linear region at low substrate concentration was used for the $K_{cat}/K_m$ ratio determination for glycolate.

Figure 2:
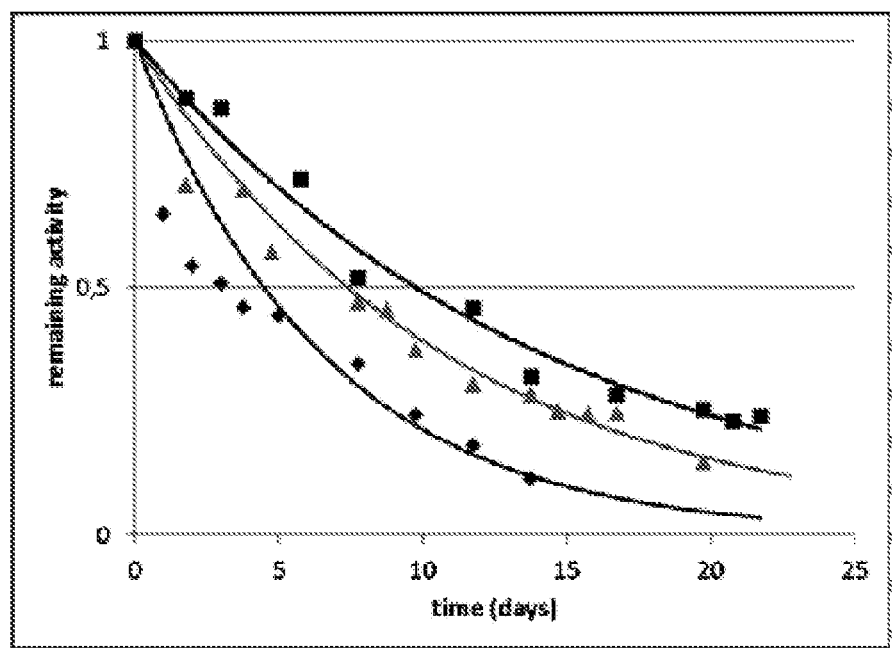
FIG. 2. A graph showing the results of a stability assay of LOD wild-type (◆), Tyr191Phe (■) and Try191Leu (▲). The activity was normalized to the starting value. The following values for the half-life of the enzymes has been determined: WT: 4.5 days; Tyr191Phe: 9.8 days and Try191Leu: 7.4 days.

Wild-type as well as mutant Ala95Gly showed substrate inhibition by glycolate (see FIG. 2), whereas L-lactate did not show any inhibition at these concentrations (0-50 mM). Substrate inhibition might also be the cause for the significantly higher substrate selectivity which was observed in preliminary measurements using not purified mutant Ala95Gly (data not shown). These activity determinations were carried out at a substrate concentration of 50 mM, which is accompanied by strong inhibition.

For the completion of characterization of the mutant, its stability was also determined as described in Example 1. The stability of mutant Ala95Gly was slightly reduced (2.3 d) in comparison to the wild type (3.8 d).

In summary, it could be shown that mutant Ala95Gly (which is already known from the prior art; see Yorita, et al., *J. Biol. Chem.* 1996 Nov. 8; 271(45):28300-5) is slightly reduced for L-lactate, but its selectivity for lactate is significantly improved. Accordingly, variants having the mutation Ala95Gly are interesting candidates for use in the determination of lactate activity, such as in biosensors and in vitro tests.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various equivalents, changes, and modifications may be made to the embodiments described herein without departing from the spirit and scope of the claimed subject matter. Thus it is intended that the specification cover the modifications and variations of the embodiments described herein provided such modifications and variations come within the scope of the appended claims and their equivalents.

What is claimed is:

1. A mutant lactate oxidase, comprising an amino acid sequence that:
   (i) has at least 90% amino acid sequence identity to the amino acid sequence of SEQ ID NO: 1 or SEQ ID NO: 2; and
   (ii) has an amino acid substitution at the position corresponding to position Tyr191 of SEQ ID NO: 1 or SEQ ID NO: 2, wherein said mutant lactate oxidase is more stable than an unsubstituted lactate oxidase comprising the amino acid sequence of SEQ ID NO: 1 or SEQ ID NO: 2, respectively, and wherein said mutant lactate oxidase catalyzes the reaction of L-lactate and oxygen ($O_2$) to form pyruvate and hydrogen peroxide ($H_2O_2$).

2. The mutant lactate oxidase of claim 1 wherein said mutant includes at least one further amino acid substitution at the position corresponding to position Gly36, Ala95, Thr103, Glu160, Val198, Asn212, Ala/Gly232, or Phe277 of SEQ ID NO: 1 or SEQ ID NO: 2.

3. The mutant lactate oxidase of claim 1, wherein tyrosine at the position corresponding to position 191 of SEQ ID NO: 1 or SEQ ID NO: 2 is substituted with a non-polar amino acid.

4. The mutant lactate oxidase of claim 3, wherein the non-polar amino acid is selected from the group consisting of: Phe, Leu, Ile, Met, and Trp.

5. The mutant lactate oxidase of claim 1, wherein said mutant lactate oxidase further includes an amino acid substitution selected from the group consisting of: Gly36Ser, Ala95Gly, Thr103Ser, Glu160Gly, Val198Ile, Asn212Asp, Ala/Gly232Ser and Phe277Tyr, wherein the amino acid numbering corresponds to the amino acid sequence of SEQ ID NO: 1 or SEQ ID NO: 2.

6. The mutant lactate oxidase of claim 1, wherein said mutant lactate oxidase further includes the amino acid substitution Ala95Gly, wherein the amino acid numbering corresponds to the amino acid sequence of SEQ ID NO: 1 or SEQ ID NO: 2.

7. The mutant lactate oxidase of claim 1, wherein said mutant lactate oxidase exhibits an increase in stability relative to the corresponding unsubstituted lactate oxidase, wherein the increase in stability of the mutant lactate oxidase relative to the corresponding unsubstituted lactate oxidase is on the order of at least: 1.5-fold; 2-fold; 2.5-fold; or 3-fold.

8. The mutant lactate oxidase of claim 6, wherein said mutant lactate oxidase exhibits an increased selectivity for lactate compared to glycolate relative to the corresponding unsubstituted lactate oxidase, the increase in selectivity for lactate compared to glycolate of the mutant lactate oxidase relative to the corresponding unsubstituted lactate oxidase is on the order of at least: 2.5-fold; 3-fold; 3.5-fold; or 4-fold increased selectivity.

9. A device, comprising said mutant lactate oxidase of claim 1.

10. The device of claim 9, wherein the device is selected from the group consisting of: a sensor, a test strip, a test element, a test strip device, and a liquid test device.

11. The device of claim 10, wherein the sensor is selected from the group of sensors consisting of: an electrochemical sensor, an optical sensor, and a test strip.

12. A kit comprising said mutant lactate oxidase of claim 1, wherein the kit includes a buffer, wherein the buffer helps to preserve the stability of said mutant lactate oxidase.

13. A method of determining the presence of lactate in a sample, comprising the steps of:
   a) contacting a sample with the mutant lactate oxidase of claim 1; and
   b) measuring at least one of the following:
      A. the amount of at least one of the following compounds produced by the mutant lactate oxidase: pyruvate or hydrogen peroxide ($H_2O_2$), and/or
      B. the amount of oxygen ($O_2$) consumed by the mutant lactate oxidase in the presence of lactate.

14. The method of claim 13, wherein the mutant lactate oxidase includes at least one further amino acid substitution at the position corresponding to position Gly36, Ala95, Thr103, Glu160, Val198, Asn212, Ala/Gly232, or Phe277 of SEQ ID NO: 1 or SEQ ID NO: 2.

15. The method of claim 13, wherein the amount of $H_2O_2$ produced by the mutant lactate oxidase is measured by following the change in a chromogen wherein the chromogen is produced by peroxidase-mediated conversion.

16. The method of claim 13, wherein the mutant lactate oxidase is part of a device selected from the group consisting of: a sensor, a test strip, a test element, a test strip device, and a liquid test device.

* * * * *

SEQUENCE LISTING

<160> NUMBER OF SEQ ID NOS: 8

<210> SEQ ID NO 1
<211> LENGTH: 276
<212> TYPE: PRT
<213> ORGANISM: Aerococcus viridians

<400> SEQUENCE: 1

```
Met Asn Asn Asn Asp Ile Glu Tyr Asn Ala Pro Ser Glu Ile Lys Tyr
1               5                   10                  15

Ile Asp Val Val Asn Thr Tyr Asp Leu Glu Glu Glu Ala Ser Lys Val
                20                  25                  30

Val Pro His Gly Gly Phe Asn Tyr Ile Ala Gly Ala Ser Gly Asp Glu
            35                  40                  45

Trp Thr Lys Arg Ala Asn Asp Arg Ala Trp Lys His Lys Leu Leu Tyr
        50                  55                  60

Pro Arg Leu Ala Gln Asp Val Glu Ala Pro Asp Thr Ser Thr Glu Ile
65                  70                  75                  80

Leu Gly His Lys Ile Lys Ala Pro Phe Ile Met Ala Pro Ile Ala Ala
                85                  90                  95

His Gly Leu Ala His Ala Thr Lys Glu Ala Gly Thr Ala Arg Ala Val
                100                 105                 110

Ser Glu Phe Gly Thr Ile Met Ser Ile Ser Ala Tyr Ser Gly Ala Thr
            115                 120                 125
```

```
Phe Glu Glu Ile Ser Glu Gly Leu Asn Gly Gly Pro Arg Trp Phe Gln
            130                 135                 140

Ile Tyr Met Ala Lys Asp Asp Gln Gln Asn Arg Asp Ile Leu Asp Glu
145                 150                 155                 160

Ala Lys Gly Asp Gly Ala Thr Ala Ile Ile Leu Thr Ala Asp Ser Thr
                165                 170                 175

Val Ser Gly Asn Arg Asp Arg Asp Val Lys Asn Lys Phe Val Tyr Pro
                180                 185                 190

Phe Gly Met Pro Ile Val Gln Arg Tyr Leu Arg Gly Thr Ala Glu Gly
            195                 200                 205

Met Ser Leu Asn Asn Ile Tyr Gly Ala Ser Lys Gln Lys Ile Ser Pro
            210                 215                 220

Arg Asp Ile Glu Glu Ile Ala Ala His Ser Gly Leu Pro Val Phe Val
225                 230                 235                 240

Lys Gly Ile Gln His Pro Glu Asp Ala Asp Met Ala Ile Lys Ala Gly
                245                 250                 255

Ala Ser Gly Ile Trp Val Ser Asn His Gly Ala Arg Gln Leu Tyr Glu
                260                 265                 270

Ala Pro Gly Ser
            275

<210> SEQ ID NO 2
<211> LENGTH: 374
<212> TYPE: PRT
<213> ORGANISM: Aerococcus viridians

<400> SEQUENCE: 2

Met Asn Asn Asp Ile Glu Tyr Asn Ala Pro Ser Glu Ile Lys Tyr
1               5                   10                  15

Ile Asp Val Val Asn Thr Tyr Asp Leu Glu Glu Glu Ala Ser Lys Val
                20                  25                  30

Val Pro His Gly Gly Phe Asn Tyr Ile Ala Gly Ala Ser Gly Asp Glu
            35                  40                  45

Trp Thr Lys Arg Ala Asn Asp Arg Ala Trp Lys His Lys Leu Leu Tyr
50                  55                  60

Pro Arg Leu Ala Gln Asp Val Glu Ala Pro Asp Thr Ser Thr Glu Ile
65                  70                  75                  80

Leu Gly His Lys Ile Lys Ala Pro Phe Ile Met Ala Pro Ile Ala Ala
                85                  90                  95

His Gly Leu Ala His Thr Thr Lys Glu Ala Gly Thr Ala Arg Ala Val
            100                 105                 110

Ser Glu Phe Gly Thr Ile Met Ser Ile Ser Ala Tyr Ser Gly Ala Thr
            115                 120                 125

Phe Glu Glu Ile Ser Glu Gly Leu Asn Gly Gly Pro Arg Trp Phe Gln
            130                 135                 140

Ile Tyr Met Ala Lys Asp Asp Gln Gln Asn Arg Asp Ile Leu Asp Glu
145                 150                 155                 160

Ala Lys Ser Asp Gly Ala Thr Ala Ile Ile Leu Thr Ala Asp Ser Thr
                165                 170                 175

Val Ser Gly Asn Arg Asp Arg Asp Val Lys Asn Lys Phe Val Tyr Pro
                180                 185                 190

Phe Gly Met Pro Ile Val Gln Arg Tyr Leu Arg Gly Thr Ala Glu Gly
            195                 200                 205

Met Ser Leu Asn Asn Ile Tyr Gly Ala Ser Lys Gln Lys Ile Ser Pro
            210                 215                 220
```

```
Arg Asp Ile Glu Glu Ile Ala Gly His Ser Gly Leu Pro Val Phe Val
225                 230                 235                 240

Lys Gly Ile Gln His Pro Glu Asp Ala Asp Met Ala Ile Lys Arg Gly
            245                 250                 255

Ala Ser Gly Ile Trp Val Ser Asn His Gly Ala Arg Gln Leu Tyr Glu
            260                 265                 270

Ala Pro Gly Ser Phe Asp Thr Leu Pro Ala Ile Ala Glu Arg Val Asn
            275                 280             285

Lys Arg Val Pro Ile Val Phe Asp Ser Gly Val Arg Arg Gly Glu His
290                 295                 300

Val Ala Lys Ala Leu Ala Ser Gly Ala Asp Val Val Ala Leu Gly Arg
305                 310                 315                 320

Pro Val Leu Phe Gly Leu Ala Leu Gly Gly Trp Gln Gly Ala Tyr Ser
                325                 330                 335

Val Leu Asp Tyr Phe Gln Lys Asp Leu Thr Arg Val Met Gln Leu Thr
            340                 345                 350

Gly Ser Gln Asn Val Glu Asp Leu Lys Gly Leu Asp Leu Phe Asp Asn
            355                 360                 365

Pro Tyr Gly Tyr Glu Tyr
    370
```

<210> SEQ ID NO 3
<211> LENGTH: 43
<212> TYPE: DNA
<213> ORGANISM: Artificial Sequence
<220> FEATURE:
<223> OTHER INFORMATION: Primer Y191Ffw

<400> SEQUENCE: 3
tcgttttccc atttggtatg ccgatcgttc aacgttactt acg                 43

<210> SEQ ID NO 4
<211> LENGTH: 43
<212> TYPE: DNA
<213> ORGANISM: Artificial Sequence
<220> FEATURE:
<223> OTHER INFORMATION: Primer Y191Frev

<400> SEQUENCE: 4
gaacgatcgg cataccaaat gggaaaacga atttattctt cac                 43

<210> SEQ ID NO 5
<211> LENGTH: 43
<212> TYPE: DNA
<213> ORGANISM: Artificial Sequence
<220> FEATURE:
<223> OTHER INFORMATION: Primer Y191Lfw

<400> SEQUENCE: 5
tcgttctccc atttggtatg ccgatcgttc aacgttactt acg                 43

<210> SEQ ID NO 6
<211> LENGTH: 43
<212> TYPE: DNA
<213> ORGANISM: Artificial Sequence
<220> FEATURE:
<223> OTHER INFORMATION: Primer Y191Lrev

<400> SEQUENCE: 6
gaacgatcgg cataccaaat gggagaacga atttattctt cac                 43

```
<210> SEQ ID NO 7
<211> LENGTH: 44
<212> TYPE: DNA
<213> ORGANISM: Artificial Sequence
<220> FEATURE:
<223> OTHER INFORMATION: Primer A95Gfw

<400> SEQUENCE: 7
ccaattggtg cccatggttt agctcacgct actaaagaag ctgg            44

<210> SEQ ID NO 8
<211> LENGTH: 45
<212> TYPE: DNA
<213> ORGANISM: Artificial Sequence
<220> FEATURE:
<223> OTHER INFORMATION: A95Grev

<400> SEQUENCE: 8
agcgtgagct aaaccatggg caccaattgg ggccatgatg aatgg           45
```